(12) United States Patent
Schadt et al.

(10) Patent No.: US 7,816,376 B2
(45) Date of Patent: Oct. 19, 2010

(54) CYCLIC AMIDES

(75) Inventors: Oliver Schadt, Rodenbach (DE);
Joachim Leibrock, Pfungstadt (DE);
Helmut Pruecher, Heppenheim (DE);
Christoph Seyfried, Seeheim Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 1056 days.

(21) Appl. No.: 10/507,581

(22) PCT Filed: Mar. 5, 2003

(86) PCT No.: PCT/EP03/02224
§ 371 (c)(1), (2), (4) Date: Sep. 13, 2004

(87) PCT Pub. No.: WO03/076420
PCT Pub. Date: Sep. 18, 2003

(65) Prior Publication Data
US 2005/0124627 A1    Jun. 9, 2005

(30) Foreign Application Priority Data
Mar. 12, 2002 (DE) .............................. 102 10 779

(51) Int. Cl.
*A61K 31/445* (2006.01)
*A61K 31/423* (2006.01)
*C07D 417/02* (2006.01)
*C07D 413/02* (2006.01)

(52) U.S. Cl. ............. 514/321; 514/253.07; 514/254.02; 514/254.06; 514/312; 514/320; 514/367; 514/375; 514/394; 544/363; 544/368; 544/373; 546/158; 546/198; 546/199; 546/201

(58) Field of Classification Search ............ 514/253.07, 514/254.02, 254.06, 312, 320, 367, 375, 514/394; 544/363, 368, 373; 546/158, 198, 546/199, 201
See application file for complete search history.

(56) References Cited

U.S. PATENT DOCUMENTS

| | | | |
|---|---|---|---|
| 4,567,187 A * | 1/1986 | Banno et al. ................. | 514/312 |
| 5,036,088 A | 7/1991 | Kitaura et al. | |
| 5,086,062 A | 2/1992 | Ando et al. | |
| 5,698,553 A | 12/1997 | Prucher et al. | |
| 7,435,744 B2 * | 10/2008 | Domany et al. ............. | 514/321 |
| 2004/0157886 A1* | 8/2004 | Domany et al. ............. | 514/317 |

FOREIGN PATENT DOCUMENTS

| | | |
|---|---|---|
| EP | 0249407 | 12/1987 |
| EP | 0360566 | 3/1990 |
| EP | 0385664 | 9/1990 |
| EP | 0709384 | 5/1996 |
| WO | WO 0192239 | 12/2001 |
| WO | WO 0194321 | 12/2001 |
| WO | WO03/010159 * | 2/2003 |

OTHER PUBLICATIONS

Chemcasts 2040186577 (2007).*
Rubini et al. "synthesis of isosteric . . . " Tetrahedron v.42, p. 6039-6045 (1986).*
Piao et al. "synthesis of 3,4- . . . " CA 132:107929 (1999).*
Piao et al. "synthesis and positive inotropic . . . " CA 132:117316 91999).*
Seddon "Pseudopolymorph . . . " Crystal growtyh and design 4(6) p. 1087 (2004) (internet print out).*
Braga et al. "Making crystal from crystals . . . " Chem. Comm p. 3635-3645 (2005).*
Domany et al. "Preparation of 2-piperidin . . . " CA 138:153539 (2003).*
Pruecher et al. "Preparation of benzylpiperidine . . . " CA 125:58339 (1996).*
Banno et al. "Preparation of piperazinylalkyl . . . " CA 137:216963 (2002).*
Masui et al. "Preparation of piperidine . . . " CA 146:100694 (2006).*
Berge "pharmaceutical salts" J. Pharm. Sci. v.66(10, p. 1-19 (1977).*
Schadt et al. "preparation of . . . " CA 139:246018 (2003).*
Schadt et al. "Preparation of aminoalkanoylamino . . . " CA 139:246018 (2003).*
Shanklin, J et al.: "Diarylmethyl-Aryloxymethylpiperidine Derivatives and Structurally Related Compounds" J Med Chem. vol. 34, No. 10, 1991 pp. 3011-3022.
Etsuo Ohshima et al.: Dibenzoxepine Derivatives As Antiallergic Agents: J Med Chem, vol. 36. No. 3, 1993 pp. 417-420.

* cited by examiner

*Primary Examiner*—Celia Chang
(74) *Attorney, Agent, or Firm*—Miller, White, Zelano, Branigan, P.C.

(57) ABSTRACT

The invention relates to compounds of the formula (I) and pharmaceutically usable derivatives, salts, solvates and stereoisomers and mixtures thereof, in which X, Y, Z, $R^1$, $R^3$, $R^4$, $R^8$, p, k, E, G, Z and Q are as defined in claim 1, which are employed as excitatory amino acid antagonists for combating neurodegenerative diseases, including cerebrovascular diseases, epilepsy, schizophrenia, Alzheimer's, Parkinson's or Huntington's disease, cerebral ischaemia, infarction or psychoses.

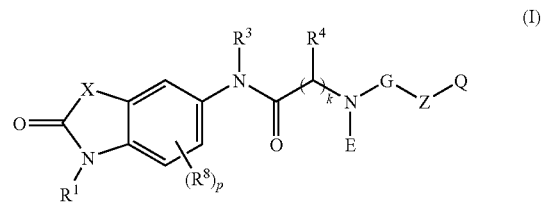

10 Claims, No Drawings

CYCLIC AMIDES

The invention relates to compounds of the formula I

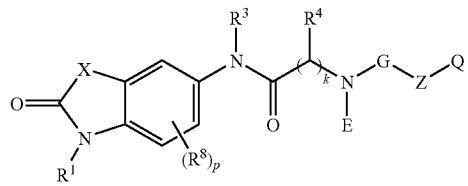

in which
R¹ is H or A
A is straight-chain or branched alkyl having from 1 to 10 carbon atoms, alkenyl having from 2 to 10 carbon atoms, alkoxy having from 1 to 10 carbon atoms or alkoxyalkyl having from 2 to 10 carbon atoms,
X is O, S, N—R², CH₂ or CH₂CH₂,
R² is H or A and
R³ is H, A, (CH₂)ₙHet, (CH₂)ₙAr or cycloalkyl having from 3 to 7 carbon atoms,
R⁴ independently is selected from H, A, cycloalkyl having from 3 to 7 carbon atoms, (CH₂)ₙNO₂, (CH₂)ₙHet, (CH₂)ₙAr, (CH₂)ₙCOR⁶, (CH₂)ₙCO(CH₂)ₘAr, (CH₂)ₙCO(CH₂)ₘHet, (CH₂)ₙCOO(CH₂)ₘAr, (CH₂)ₙCOO(CH₂)ₘHet, (CH₂)ₙOR⁶, (CH₂)ₙO(CH₂)ₘAr, (CH₂)ₙO(CH₂)ₘHet, (CH₂)ₙSR⁶, (CH₂)ₙS(CH₂)ₘAr, (CH₂)ₙS(CH₂)ₘHet, (CH₂)ₙN(R⁶)(CH₂)ₘAr, (CH₂)ₙN(R⁶)(CH₂)ₘHet, (CH₂)ₙSO₂N(R⁶)(CH₂)ₘAr, (CH₂)ₙN(R⁶)SO₂(CH₂)ₘAr, (CH₂)ₙSO₂N(R⁶)(CH₂)ₘHet, (CH₂)ₙN(R⁶)SO₂(CH₂)ₘHet, (CH₂)ₙCON(R⁶)(CH₂)ₘAr, (CH₂)ₙN(R⁶)CO(CH₂)ₘAr, (CH₂)ₙCON(R⁶)(CH₂)ₘHet, (CH₂)ₙN(R⁶)CO(CH₂)ₘHet, (CH₂)ₙN(R⁶)₂, CH=N—OA, CH₂CH=N—OA, (CH₂)ₙNHOA, (CH₂)ₙ(R⁶)Het, (CH₂)ₙCH=N-Het, (CH₂)ₙOCOR⁶, (CH₂)ₙOC(O)N(R⁶)₂, (CH₂)ₙOC(O)NR⁶(CH₂)ₘAr, (CH₂)ₙOC(O)NR⁶(CH₂)ₘHet, (CH₂)ₙNR⁶COOR⁶, (CH₂)ₙNR⁶COO(CH₂)ₘAr, (CH₂)ₙNR⁶COO(CH₂)ₘHet, (CH₂)ₙN(R⁶)CH₂CH₂OR⁶, (CH₂)ₙN(R⁶)CH₂CH₂OCF₃, (CH₂)ₙN(R⁶)C(R⁶)HCOOR⁶, (CH₂)ₙN(R⁶)CH₂COHet, (CH₂)ₙN(R⁶)CH₂Het, (CH₂)ₙN(R⁶)CH₂CH₂N(R⁶)CH₂COOR⁶, (CH₂)ₙN(R⁶)CH₂CH₂N(R⁶)₂, CH=CHCOOR⁶, CH=CHCH₂NR⁶Het, CH=CHCH₂N(R⁶)₂, CH=CHCH₂OR⁶, (CH₂)ₙN(COOR⁶)COOR⁶, (CH₂)ₙN(CONH₂)COOR⁶, (CH₂)ₙN(CONH₂)CONH₂, (CH₂)ₙN(CH₂COOR⁶)COOR⁶, (CH₂)ₙN(CH₂CONH₂)COOR⁶, (CH₂)ₙN(CH₂CONH₂)CONH₂, (CH₂)ₙCH R⁶COR⁶, (CH₂)ₙCH R⁶COOR⁶, (CH₂)ₙCHR⁶CH₂OR⁶, (CH₂)ₙOCN or (CH₂)ₙNCO and
R⁶ is H, A or cycloalkyl having from 3 to 7 carbon atoms, and
k is 1 or 2,
E is H, A, (CH₂)ₙHet, (CH₂)ₙAr or cycloalkyl having from 3 to 7 carbon atoms,
G is an optionally substituted alkylene radical having from 1 to 4 carbon atoms, where the substituents are selected from the meanings indicated for R⁴, or
E and
G, together with the N atom to which they are bonded, are a 5-, 6- or 7-membered heterocyclic radical, which can have 1 or 2 further hetero atoms selected from N, O and S,
Z is O, S, N—R¹⁵, CH₂ or CH₂CH₂, R¹⁵ is H, A, (CH₂)ₙHet, (CH₂)ₙAr or cycloalkyl having from 3 to 7 carbon atoms,
Het is a saturated, unsaturated or aromatic mono- or bicyclic heterocyclic radical which is unsubstituted or mono- or poly-substituted by A, Hal, NO₂, CN, OR⁶, N(R⁶)₂, COOR⁶, CON(R⁶)₂, NR⁶COR⁶, NR⁶CON(R⁶)₂, NR⁶SO₂A, COR⁶, SO₂NR⁶, S(O)ᵥA and/or OOCR⁶,
Ar is an aromatic hydrocarbon radical having from 6 to 14 carbon atoms which is unsubstituted or mono- or poly-substituted by A, Hal, NO₂, CN, OR⁶, N(R⁶)₂, COOR⁶, CON(R⁶)₂, NR⁶COR⁶, NR⁶CON(R⁶)₂, NR⁶SO₂A, COR⁶, SO₂NR⁶, S(O)ᵥA and/or OOCR⁶,
p is 0, 1, 2 or 3
w is 0, 1, 2 or 3 and
Hal is F, Cl, Br or I, and
Q is a 5- or 6-membered, polyethylenically unsaturated or aromatic carbocyclic or heterocyclic radical, which be mono- or polysubstituted, where the substituents are selected, independently of one another, from the meanings of R⁴ other than H, and where the heterocyclic radical can contain from 1 to 4 hetero atoms, selected, independently of one another, from N, O and S, and pharmaceutically usable derivatives, solvates and stereoisomers thereof, including mixtures thereof in all ratios, and in particular salts and solvates thereof.

Benzylpiperidine derivatives with high affinity to binding sites of amino acid receptors are disclosed, for example, in EP 0 709 384 A1.

The invention had the object of finding novel compounds having valuable properties, in particular those which have an improved action profile, for example higher activity, higher selectivity or a broader use profile and/or less severe side effects. It should preferably be possible to prepare the novel compounds simply and inexpensively, and they should be, in particular, suitable for the preparation of medicaments.

Surprisingly, it has been found that the object is achieved by the compounds of the formula I. In particular, it has been found that the compounds of the formula I and salts thereof have very valuable pharmacological properties as well as being well tolerated. In particular, they exhibit particularly high affinity to binding sites of amino acid receptors, in particular to the ifenprodil binding site on the NMDA receptor (NMDA=N-methyl D-aspartate), which allosterically modulates the polyamine binding site. The compounds according to the invention are preferably ligands of the ifenprodil binding site of the NMDA receptor and thus belong to the area of the NR2B antagonists. The compounds according to the invention are particularly preferably ligands of the ifenprodil binding site of the NMDA-2B receptor.

The binding test for [³H]-ifenprodil can be carried out by the method of Schoemaker et al., Eur. J. Pharmacol. 176, 249-250 (1990).

The compounds are suitable for the treatment of neurodegenerative diseases, including cerebrovascular diseases. The novel compounds can likewise be used as analgesic or anxiolytic and for the treatment of epilepsy, schizophrenia, Alzheimer's disease, Parkinson's disease, Huntington's disease, cerebral ischaemia or infarction. They are furthermore suitable for the treatment of psychoses caused by excessively high amino acid levels.

The [³H]-CGP-39653 binding test for the glutamate binding site of the NMDA receptor can be carried out, for example, by the method of M. A. Stills et al., described in Eur. J. Pharmacol. 192, 19-24 (1991). The test for the glycine binding site of the NMDA receptor can be carried out by the method of M. B. Baron et al., described in Eur. J. Pharmacol. 206, 149-154 (1991).

The action against Parkinson's disease, i.e. potentiation of the L-DOPA-induced contralateral rotation in hemiparkinsonian rats, can be demonstrated by the method of U. Ungerstedt and G. W. Arbuthnott, Brain Res. 24, 485 (1970).

The compound is particularly suitable for the treatment or prophylaxis of strokes and for protection against and treatment of cerebral oedema and states of undersupply of the central nervous system, in particular hypoxia or anoxia.

The said effects can in addition be demonstrated or checked by the methods as described in the following references:

J. W. McDonald, F. S. Silverstein and M. V. Johnston, Eur. J. Pharmacol. 140, 359 (1987); R. Gill, A. C. Foster and G. N. Woodruff, J. Neurosci. 7, 3343 (1987); J. B. Bederson et al., Stroke, 17, 472-476 (1986); S. Brint et al., J. Cereb. Blood Flow Metab. 8, 474-485 (1988).

The references listed below disclose various antagonists which are able to block various binding sites of the NMDA receptor:

W. Danysz, C. G. Parsons, I. Bresink and G. Quack, Drug, News & Perspectives 8, 261 (1995), K. R. Gee, Exp. Opin. Invest. Drugs 3, 1021 (1994) and J. J. Kulagowski and L. L. Iversen, J. Med. Chem. 37, 4053 (1994).

Ifenprodil and eliprodil of the formulae III and IV respectively are able to block the NMDA receptor by interacting with the modulatory polyamine binding site (C. J. Carter, K. G. Lloyd, B. Zivkovic and B. Scatton, J. Pharmacol. Exp. Ther. 253, 475 (1990)).

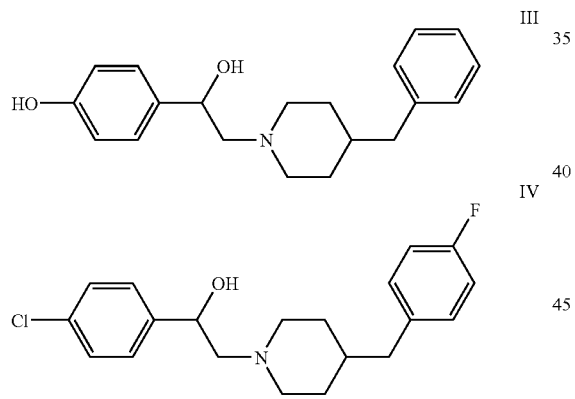

Since ifenprodil and eliprodil interact with the polyamine binding site on the NMDA receptor, the antagonistic activity of the compounds according to the invention can be determined in a spermine-stimulated [$^3$H]MK-801 (dizocilpine) binding test.

In the presence of saturation concentrations of glycine and NMDA, spermine is able further to increase the binding of MK-801, which is inhibited by ifenprodil, eliprodil and very particularly effectively by the compounds according to the invention.

In addition, the compounds according to the invention can be tested in a [$^3$H]GABA (γ-aminobutyric acid) liberation test, analogously to J. Dreijer, T. Honore and A. Schousboe, J. Neurosci. 7, 2910 (1987), which, as an in-vitro model, describes the antagonistic function in the cell.

The invention accordingly relates to the compounds of the formula I according to claim 1 and/or pharmaceutically usable derivatives, solvates and stereoisomers thereof, including mixtures thereof in all ratios, and in particular physiologically acceptable salts thereof, as antagonists to receptors of excitatory amino acids, such as, for example, glutamic acid, and salts thereof.

The invention relates to the compounds of the formula I according to claim 1 and/or pharmaceutically usable derivatives, solvates and stereoisomers thereof, including mixtures thereof in all ratios, and in particular physiologically acceptable salts thereof, as glycine transporter inhibitors.

In particular, the invention relates to the compounds of the formula I according to claim 1 and/or pharmaceutically usable derivatives, solvates and stereoisomers thereof, including mixtures thereof in all ratios, and in particular physiologically acceptable salts thereof, as excitatory amino acid antagonists for combating neurodegenerative diseases, including cerebrovascular diseases, epilepsy, schizophrenia, Alzheimer's disease, Parkinson's disease, Huntington's disease, cerebral ischaemia, infarction or psychoses.

The invention also relates to the use of the compounds of the formula I according to claim 1 and/or pharmaceutically usable derivatives, solvates and stereoisomers thereof, including mixtures thereof in all ratios, and in particular physiologically acceptable salts thereof, for the preparation of a medicament for combating neurodegenerative diseases, including cerebrovascular diseases, epilepsy, schizophrenia, Alzheimer's disease, Parkinson's disease, Huntington's disease, cerebral ischaemia, infarction or psychoses.

In this connection, reference is made to WO00/00197, the disclosure content of which in its full scope is incorporated herein by way of reference.

The compounds of the formula I can be employed as medicament active ingredient in human and veterinary medicine.

The invention furthermore relates to a process for the preparation of the compounds of the formula I according to claim 1 and physiologically acceptable salts thereof, characterised in that a) a compound of the formula II

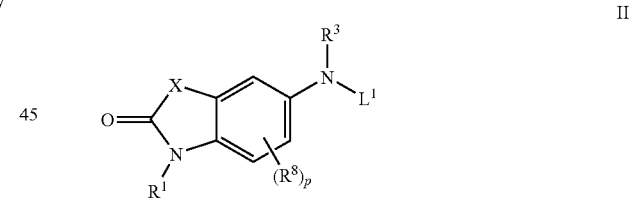

in which $L^1$ is H or a metal ion, and $R^1$, X, $R^3$, $R^8$ and p are as defined above and below, b) is reacted with a compound of the formula V

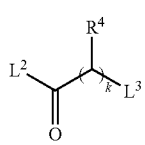

in which $L^2$ is Cl, Br, I, OH or a reactively esterified OH group, $L^3$ is Cl, Br, I, OH or a diazonium group and $R^4$ and k are as defined above and below, and c) with a compound of the formula VI

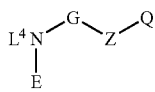
VI in which
L4 is H or a metal ion and E, G, Z, and Q are as defined above and below,
and, if desired,
d) the resultant compound of the formula I is converted into one of its salts by treatment with an acid.

In a preferred embodiment, the compound of the formula VI is selected from compounds of the formulae

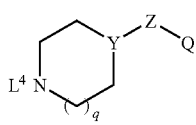 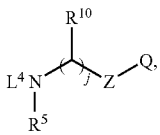

in which $L^4$, q, Y, $R^5$, $R^{10}$, Z, j and Q are as defined above and below.

The compound of the formula VI is preferably selected from compounds of the formulae

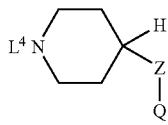 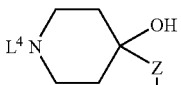

and

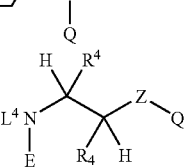

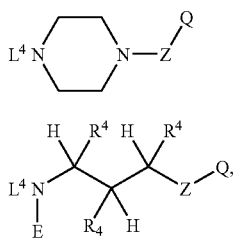

in which $L^4$, $R^4$, Z, Q and E are as defined above and below.

The compound of the formula VI is preferably selected from compounds of the formulae

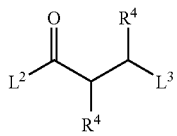 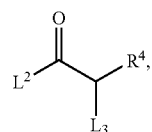

in which $L^2$ $L^3$ and $R^4$ are as defined above and below.

The process according to the invention can be carried out as a one-pot reaction, i.e. isolation and/or purification steps are omitted as far as possible and only the desired end product, i.e. generally a compound according to the invention or a pharmaceutically usable derivative thereof, is purified and/or isolated. Alternatively, a purification and/or isolation step can be carried out after each of the said reaction steps. Mixed forms of the procedures described above are also conceivable. Suitable purification and isolation steps are known to the person skilled in the art, for example from Houben-Weyl, Methoden der organischen Chemie [Methods of Organic Chemistry], Georg-Thieme-Verlag, Stuttgart.

The invention relates, in particular, to the compounds of the formula I in which at least one of the said radicals has one of the preferred meanings indicated above or below.

For the purposes of the present invention, alkyl is a linear or branched alkyl radical, preferably an unbranched alkyl radical, which has 1, 2, 3, 4, 5, 6, 7, 8, 9 or 10 carbon atoms, preferably 1, 2, 3, 4 or 5 carbon atoms, and may be mono- or poly[lacuna] by halogen (Hal), for example perfluorinated. If an alkyl radical is substituted by halogen, it preferably, depending on the number of carbon atoms of the alkyl radical, has 1, 2, 3, 4 or 5 halogen atoms. Thus, for example, a methyl group (alkyl radical having 1 carbon atom) can be mono-, di- or trisubstituted by halogen, and an ethyl group (alkyl radical having 2 carbon atoms) can be mono-, di-, tri-, tetra- or pentasubstituted by halogen.

For alkyl groups having more than 2 carbon atoms, the same preferably applies as for ethyl groups. Alkyl is particularly preferably methyl, ethyl, trifluoromethyl, pentafluoroethyl or propyl, furthermore preferably isopropyl, butyl, isobutyl, sec-butyl or tert-butyl, but also n-pentyl, neopentyl, isopentyl or hexyl.

The term "alkylene" is preferably a divalent carbon radical preferably having from 1 to 10 carbon atoms and in particular from 1 to 6 carbon atoms, which may optionally be mono- or polysubstituted. Suitable substituents for alkylene radicals are, for example, halogen, hydroxyl groups, alkyl radicals, alkoxy radicals, amino groups and alkylamino groups. Alkylene is preferably methylene, ethylene, n-propylene and n-butylene.

The term "alkenyl" preferably covers mono- or polyethylenically unsaturated, straight-chain or branched hydrocarbon radicals having from 2 to 10 and in particular from 3 to 6 carbon atoms, and in particular allyl, 2- or 3-butenyl, isobutenyl, sec-butenyl, furthermore preferably 4-pentenyl, isopentenyl or 5-hexenyl.

The term "alkoxy" is preferably radicals of the formula —O-alkyl, in which alkyl is as defined above, or, if two alkoxy radicals are bonded to adjacent (vicinal) carbon atoms, "alkoxy" is preferably —O-alkylene-O—, in which alkylene is as defined above. Preferred alkoxy radicals of the formula —O-alkyl are methoxy, ethoxy and propoxy. Preferred alkoxy radicals of the formula —O-alkylene-O— are —O—CH$_2$—O—, —O—CH$_2$CH$_2$—O— and —O—CH$_2$CH$_2$CH$_2$—O—.

The term "alkoxyalkyl" preferably covers straight-chain radicals of the formula $C_uH_{2u+1}$—O—$(CH_2)_v$, in which u and v are each, independently of one another, from 1 to 6. Particularly preferably, u=1 and v=1 to 4.

The term "aryl" preferably covers an unsubstituted or mono- or polysubstituted benzene ring, for example an unsubstituted or substituted phenyl radical or an unsubstituted or mono- or polysubstituted system of benzene rings, such as, for example, anthracene, phenanthrene or naphthalene ring systems. Examples of suitable substituents include alkyl, alkoxy, oxo, hydroxyl, mercapto, amino, nitro, cyano and halogen radicals.

The term "aralkyl" preferably covers an aryl radical as defined above bonded to an alkyl radical as defined above. Examples of suitable aralkyl radicals include, but are not restricted to, benzyl, phenylpropyl, phenylbutyl and the like.

Ar is preferably an aryl radical which is unsubstituted or mono- or polysubstituted by A, Hal, NO$_2$, CN, OR$^6$, N(R$^6$)$_2$, COOR$^6$, CON(R$^6$)$_2$, NR$^6$COR$^6$, NR$^6$CON(R$^6$)$_2$, NR$^6$SO$_2$A, COR$^6$, SO$_2$NR$^6$, S(O)$_w$A and/or OOCR$^6$, and in particular phenyl, naphthyl or biphenyl, each of which is unsubstituted or substituted as above.

Het is preferably a heteroaromatic radical which is unsubstituted or substituted by A and/or Hal and in particular a saturated heterocyclic radical which is unsubstituted or substituted by A and/or Hal. Het is preferably 1-piperidyl, 1-piperazyl, 1-(4-methyl)piperazyl, 4-methylpiperazin-1-ylamine, 4-morpholinyl, 1-pyrrolidinyl, 1-pyrazolidinyl 1-(2-methyl)pyrazolidinyl, 1-imidazolidinyl or 1-(3-methyl)imidazolidinyl, thiophen-2-yl or thiophen-3-yl, 2-, 3- or 4-pyridyl, which may be unsubstituted or substituted by one or more CN group, 2-, 4- or 5-oxazolyl, 2-, 4- or 5-thiazolyl, quinolinyl, isoquinolinyl, 2- or 4-pyridazyl, 2-, 4- or 5-pyrimidyl, 2- or 3-pyrazinyl.

The radical Q is a 5- or 6-membered, polyethylenically unsaturated or aromatic carbocyclic radical, which may be mono- or polysubstituted, preferably mono- to trisubstituted, where the substituents are selected, independently of one another, from the meanings of R$^4$ other than H, or are preferably selected from A, in particular alkyl having from 1 to 6 carbon atoms, alkoxy having from 1 to 6 carbon atoms and alkoxyalkyl having from 2 to 6 carbon atoms, Hal, in particular F and Cl, NO$_2$, OR$^6$, N(R$^6$)$_2$, CN, COOR$^6$, CON(R$^6$)$_2$, NR$^6$COR$^6$, NR$^6$CON(R$^6$)$_2$, NR$^6$SO$_2$A, COR$^6$, SO$_2$NR$^6$, S(O)$_w$A, OOCR$^6$ and C(NH)NOH. Examples of carbocyclic radicals Q are cyclopentadienyl, cyclohexadienyl, phenyl, naphthyl, in particular 1-naphthyl and 2-naphthyl, and biphenyl, each of which may be substituted as described above/below. The carbocyclic radical Q is preferably phenyl and preferably substituted phenyl, in particular 4-alkylphenyl, such as 4-tolyl(4-methylphenyl), 4-alkoxyphenyl, such as 4-methoxyphenyl, 3,4-dialkoxyphenyl, such as 3,4-dimethoxyphenyl and 3,4-methylenedioxyphenyl, and 4-halophenyl, such as 4-fluorophenyl and 4-chlorophenyl.

The radical Q is alternatively a 5- or 6-membered, polyethylenically unsaturated or aromatic heterocyclic radical, which may contain from 1 to 4 hetero atoms, selected, independently of one another, from N, O and S, and which may be mono- or polysubstituted, preferably mono- to trisubstituted, where the substituents are selected, independently of one another, from the meanings of R$^4$ other than H, or are preferably selected from A, in particular alkyl having from 1 to 6 carbon atoms, alkoxy having from 1 to 6 carbon atoms and alkoxyalkyl having from 2 to 6 carbon atoms, Hal, in particular F and Cl, NO$_2$, OR$^6$, N(R$^6$)$_2$, CN, COOR$^6$, CON(R$^6$)$_2$, NR$^6$COR$^6$, NR$^6$CON(R$^6$)$_2$, NR$^6$SO$_2$A, COR$^6$, SO$_2$NR$^6$, S(O)$_w$A, OOCR$^6$ and C(NH)NOH. Examples of heterocyclic radicals Q are furanyl, thiophenyl, pyrrolyl, imidazolyl, pyrazolyl, triazolyl, tetrazolyl, thiazolyl, oxazolyl, isoxazolyl, oxadiazolyl, oxopyridyl, thiadiazolyl, isothiazolyl, pyridyl, pyridazyl, pyrazinyl, pyrimidyl, quinolinyl, isoquinolinyl, benzofuranyl, benzothiophenyl, indolyl and indazolyl, each of which may be substituted as described above/below. The heterocyclic radical Q is preferably optionally substituted furanyl, thiophenyl, pyrrolyl, pyridyl, pyridazyl, pyrazinyl and pyrimidyl.

In the compounds of the formula I and the compounds of the formula VI, the group Z-Q is preferably selected from the groups

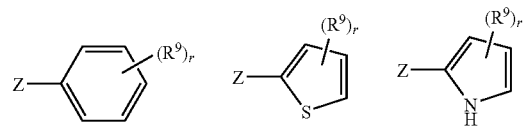

in which
R$^9$ independently is selected from Hal, A, (CH$_2$)$_n$Het, (CH$_2$)$_n$Ar, (CH$_2$)$_n$COO(CH$_2$)$_m$Ar, (CH$_2$)$_n$COO(CH$_2$)$_m$Het, (CH$_2$)$_n$OR$^6$, (CH$_2$)$_n$O(CH$_2$)$_m$Ar, (CH$_2$)$_n$O(CH$_2$)$_m$Het, (CH$_2$)$_n$N(R$^6$)(CH$_2$)$_m$Ar, (CH$_2$)$_n$N(R$^6$)(CH$_2$)$_m$Het, (CH$_2$)$_n$SO$_2$N(R$^6$)(CH$_2$)$_m$Ar, (CH$_2$)$_n$N(R$^6$)SO$_2$(CH$_2$)$_m$Ar, (CH$_2$)$_n$SO$_2$N(R$^6$)(CH$_2$)$_m$Het, (CH$_2$)$_n$N(R$^6$)SO$_2$(CH$_2$)$_m$Het, (CH$_2$)$_n$N(R$^6$)$_2$, (CH$_2$)$_n$NHOA, (CH$_2$)$_n$(R$^6$)Het, (CH$_2$)$_n$OCOR$^6$, (CH$_2$)$_n$OC(O)N(R$^6$)$_2$, (CH$_2$)$_n$OC(O)NR$^6$(CH$_2$)$_m$Ar, (CH$_2$)$_n$OC(O)NR$^6$(CH$_2$)$_m$Het, (CH$_2$)$_n$NR$^6$COOR$^6$, (CH$_2$)$_n$NR$^6$COO(CH$_2$)$_m$Ar, (CH$_2$)$_n$ NR$^6$COO(CH$_2$)$_m$Het, and in particular, independently of one another, is Hal, NO$_2$, OR$^6$, N(R$^6$)$_2$, CN, COOR$^6$, CON(R$^6$)$_2$, NR$^6$COR$^6$, NR$^6$CON(R$^6$)$_2$, NR$^6$SO$_2$A, COR$^6$, SO$_2$NR$^6$, S(O)$_w$A, OOCR$^6$ and/or C(NH)NOH, w is 0, 1, 2 or 3, and
r is 0, 1, 2, 3, 4 or 5 and in particular 0, 1, 2 or 3.
If the group Z-Q is the group

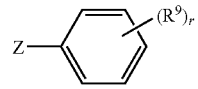

it is preferably selected from the groups

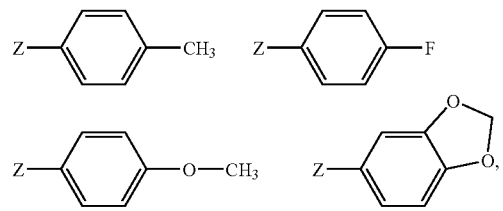

in which Z is as defined above.
In the compounds of the formula I, the group

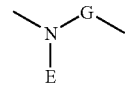

is preferably selected from the groups

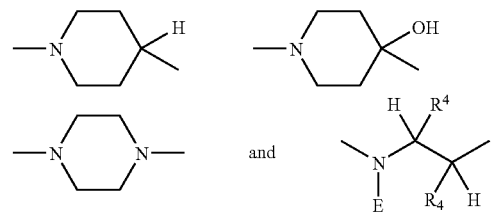

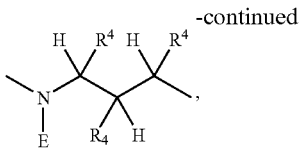

in which $R^4$ and E is as defined above and below.

A preferred embodiment of the present invention relates to compounds of the formula I in which $R^1$, X, $R^3$, $R^8$, p, $R^4$, k and Z are as defined above and below, and E and G, together with the N atom to which they are bonded, are a 5-, 6- or 7-membered heterocyclic radical, which may have 1 or 2 further hetero atoms selected from N, O and S, and in which Q is selected from substituted or unsubstituted phenyl radicals, preferably substituted phenyl radicals, and substituted or unsubstituted thiophen-2-yl radicals, preferably unsubstituted thiophen-2-yl radicals. In this embodiment, X is preferably O, $R^1$ and $R^3$ are preferably H or A, and k is preferably 1 or 2 and in particular 1. In this embodiment, $R^4$ is preferably independently aryl, H or A particularly preferably H, methyl or phenyl and in particular H.

Preferred compounds of the formula I are compounds of the formula Ia

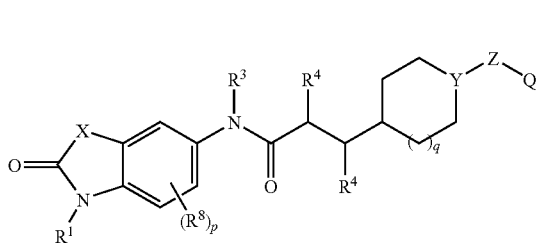

in which $R^1$, X, $R^3$, $R^8$, p, Z and Q are as defined above and below, and the two radicals $R^4$ are selected, independently of one another, from the meanings for $R^4$ indicated above and below, and in which
q is 0, 1, 2 or 3,
Y is CH, $COR^7$, $CSR^7$, or N, and
$R^7$ is H, A, $(CH_2)_n$Het, $(CH_2)_n$Ar or cycloalkyl having from 3 to 7 carbon atoms, and pharmaceutically usable derivatives, solvates and stereoisomers thereof, including mixtures thereof in all ratios, and in particular salts and solvates thereof.

Preferred compounds of the formula I are compounds of the formula Ib

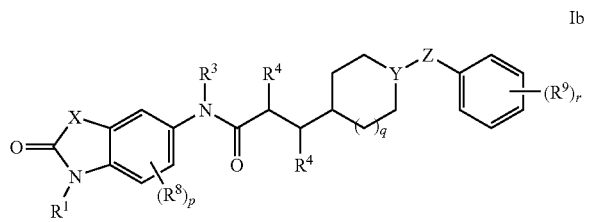

in which the radicals
$R^9$ independently are selected from the meanings of $R^4$ other than H, or, independently of one another, are Hal, $NO_2$, $OR^6$, $N(R^6)_2$, CN, $COOR^6$, $CON(R^6)_2$, $NR^6COR^6$, $NR^6CON(R^6)_2$, $NR^6SO_2A$, $COR^6$, $SO_2NR^6$, $S(O)_wA$, $OOCR^6$ and/or C(NH)NOH,
r is 0, 1, 2, 3, 4 or 5,
and in which $R^1$, $R^2$, $R^3$, $R^4$, $R^8$, p, q, X, Y and Z are as defined above and below, and the pharmaceutically usable derivatives, solvates and stereoisomers thereof, including mixtures thereof in all ratios, and in particular salts and solvates thereof.

The present invention preferably relates to compounds of the formula I, Ia and in particular compounds of the formula Ib as described above, in which $R^1$, $R^2$, $R^8$, r, Ar and Het are as defined above and in which A is straight-chain alkyl having from 1 to 4 carbon atoms, branched alkyl having from 3 to 6 carbon atoms, alkoxy having from 1 to 4 carbon atoms, X is O or N—$R^2$, and $R^3$ is H or A, $R^4$, independently of one another, are selected from H, A, $(CH_2)_n$Het, $(CH_2)_n$Ar, $(CH_2)_n$COO$(CH_2)_m$Ar, $(CH_2)_n$COO$(CH_2)_m$Het, $(CH_2)_n$$OR^6$, $(CH_2)_n$O$(CH_2)_m$Ar, $(CH_2)_n$O$(CH_2)_m$Het, $(CH_2)_n$N$(R^6)(CH_2)_m$Ar, $(CH_2)_n$N$(R^6)(CH_2)_m$Het, $(CH_2)_n$SO$_2$N$(R^6)(CH_2)_m$Ar, $(CH_2)_n$N$(R^6)$SO$_2(CH_2)_m$Ar, $(CH_2)_n$SO$_2$N$(R^6$ $(CH_2)_m$Het, $(CH_2)_n$ N$(R^6)$SO$_2(CH_2)_m$Het, $(CH_2)_n$N$(R^6)_2$, $(CH_2)_n$NHOA, $(CH_2)_n$$(R^6)$Het, $(CH_2)_n$OCOR$^6$, $(CH_2)_n$OC(O)N$(R^6)_2$, $(CH_2)_n$OC(O)NR$^6(CH_2)_m$Ar, $(CH_2)_n$OC(O)NR$^6(CH_2)_m$ Het, $(CH_2)_n$NR$^6$COOR$^6$, $(CH_2)_n$NR$^6$COO $(CH_2)_m$Ar, $(CH_2)_n$NR$^6$COO$(CH_2)_m$Het, and $R^6$ is H or A,
Y is CH, $COR^7$ or N,
$R^7$ is H, A, $(CH_2)_n$Het or $(CH_2)_n$Ar,
Z is O, $CH_2$ or $CH_2CH_2$,
n, m, independently of one another, are 0, 1, 2 or 3,
p is 0, 1 or 2
q is 1 or 2 and
$R^9$ independently are selected from the meanings of $R^4$ other than H or, independently of one another, are F, Cl, Br, I, CN, $NO_2$, $NH_2$, $CF_3$, $OCF_3$, C(NH)NOH and $SO_2CH_3$.

and solvates and salts thereof.

The sum of n and m is preferably greater than zero.

Some preferred groups of compounds of the formulae I, Ia and/or Ib can be expressed by the following sub-formulae Iα) to Iζ), which conform to the formula I and/or Ia and in particular to the formula Ib and in which the radicals not designated in greater detail are as defined above, but in which in Iα) $R^1$ is H or methyl;
in Iβ) $R^1$ is H or methyl and
  X is O, S or $NR^2$ and in particular O;
in Iγ) $R^1$ is H or methyl,
  X is O, S or $NR^2$ and in particular O,
  $R^2$ is H,
  $R^3$ is H or A and in particular H or methyl, and
  $R^9$ is Hal;
in Iδ) $R^1$ is H or methyl,
  X is O, S or $NR^2$ and in particular O,
  $R^2$ is H,
  $R^3$ is H or A and in particular H or methyl,
  Y is CH, $COR^7$ or N, and
  $R^9$ is Hal, alkyl or alkoxy;
in Iε) $R^1$ is H or methyl,
  X is O, S or $NR^2$ and in particular O,
  $R^2$ is H, R³ is H or A and in particular H or methyl,
Y is CH, COR⁷ or N and in particular CH,
R⁷ is H,
Z is O, CH₂, CH₂CH₂ or N—R¹⁵,
R¹⁵ is H or A,
R⁸ is Hal or A and in particular Cl, and
p is 0 or 1;
in Iζ) R¹ is H or methyl,
X is O, S or NR² and in particular O,
R² is H,
R³ is H or A and in particular H or methyl,
Y is CH, COR⁷ or N and in particular CH,
R⁷ is H,
Z is O, CH₂, CH₂CH₂ or N—R¹⁵,
R¹⁵ is H or A,
R⁸ is Hal or A and in particular Cl,
p is 0 or 1, and
R⁹ is Hal, alkyl or alkoxy.

In an embodiment of the present invention, n is 0 or 1 and in particular 0.

A preferred embodiment of the present invention relates to compounds in which one radical R⁴ or both radicals R⁴ are H.

In a preferred embodiment of the present invention and in particular in the sub-formulae Iα) to Iζ), the radical R⁸ is A, Hal, in particular F or Cl, CN, NO₂ NH₂, CF₃, OCF₃ or SO₂CH₃, particularly preferably A or Cl; and p is 0, 1 or 2, particularly preferably 0 or 1.

In a preferred embodiment of the present invention, the radical R³⁹ in the formula Ia and in particular in the sub-formulae Iα) to Iε) is A, F, Cl, Br, I, CN, NO₂, NH₂, CF₃, OCF₃ or SO₂CH₃.

In a particularly preferred embodiment of the present invention, the radical R³⁹ in the formula Ia and in particular in the sub-formulae Iα) to Iζ) is F and in particular F in the 4-position, substituted or preferably unsubstituted alkyl having from 1 to 4 carbon atoms, particularly preferably alkyl as defined above in the 4-position, very particularly preferably methyl and in particular 4-methyl, or alkoxy, preferably unsubstituted alkoxy having from 1 to 3 carbon atoms, where r is preferably 0, 1, 2 or 3 and particularly preferably 1 or 2. In this embodiment, alkoxy is preferably methoxy if only one of the radicals R³⁹ is alkoxy and in particular if R³⁹ is alkoxy and r is 1.

In this embodiment, alkoxy is preferably —O-alkylene-O— having from 1 to 3 carbon atoms and in particular —O—CH₂—O— or —O—CH₂CH₂—O— if two of the radicals R³⁹ are alkoxy and in particular if two radicals R³⁹ are alkoxy and r is 2. In this stands embodiment, one of the radicals R³⁹ is preferably in the 4-position.

In a preferred embodiment of the present invention and in particular in the sub-formulae Iα) to Iζ), the radicals R⁴ are, independently of one another, preferably H, methyl, ethyl, trifluoromethyl, pentafluoroethyl, propyl, isopropyl, butyl, isobutyl, sec-butyl or tert-butyl, particularly preferably H, methyl, ethyl, trifluoromethyl, pentafluoroethyl and in particular H or methyl.

In a specific and preferred embodiment, the present invention relates to a compound of the formula I and in particular a compound of the formula Ia in which X is O, and pharmaceutically usable derivatives, solvates, salts, stereoisomers and mixtures thereof and in particular the solvates and salts of the compounds.

In a further specific and preferred embodiment, the present invention relates to a compound of the sub-formulae Iα) to Iζ) as defined above in which X is O, pharmaceutically usable derivatives, solvates, salts, stereoisomers and mixtures thereof and in particular the solvates and salts of the compounds.

In a further preferred embodiment, the present invention relates to a compound of the formula I, preferably a compound of the formula Ia and in particular a compound of the sub-formulae Iα) to Iγ) in which Y is CH, CHOH (i.e. COR⁷ in which R⁷ is H) or N and in particular CH, and solvates and salts thereof.

In a further preferred embodiment of the present invention, the group

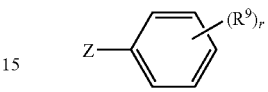

in the compounds of the formula Ib and in particular in the sub-formulae Iα) to Iζ) is selected from the groups

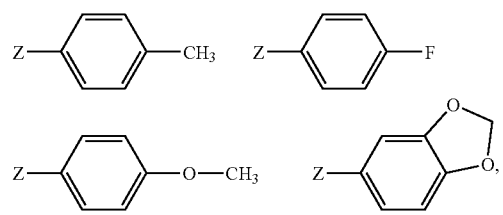

in which Z is as defined above.

In a very particularly preferred embodiment, the present invention relates to a compound of the formula I, preferably of the formula Ia, particularly preferably of the formula Ib and in particular a compound of the sub-formulae Iα) to Iζ), which comprises the features of one or more of the embodiments described above and in particular the features of all the embodiments described above.

In a very particularly preferred embodiment of the present invention, the compounds of the formula I are selected from a)

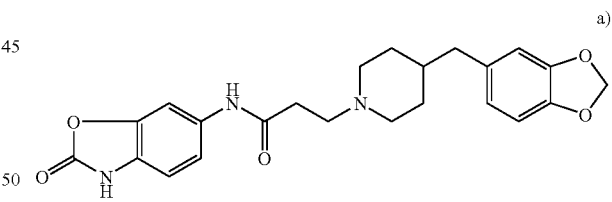

3-[4-(3,4-methylenedioxybenzyl)piperidino]-N-(2-oxo-2,3-dihydrobenzoxazol-6-yl)propionamide b)

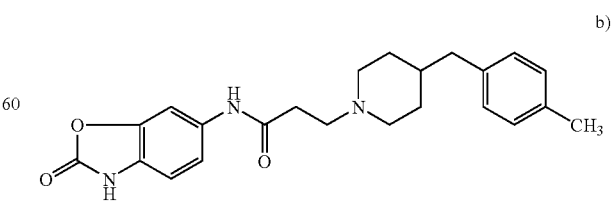

3-[4-(4-methylbenzyl)piperidino]-N-(2-oxo-2,3-dihydrobenzoxazol-6-yl)propionamide c)

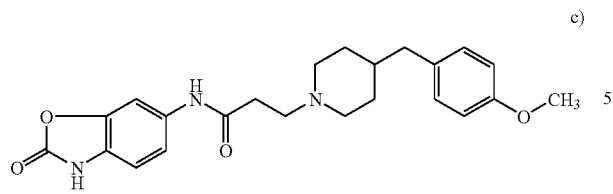

3-[4-(4-methoxybenzyl)-1-piperidyl]-N-(2-oxo-2,3-dihydrobenzoxazol-6-yl)propionamide d)

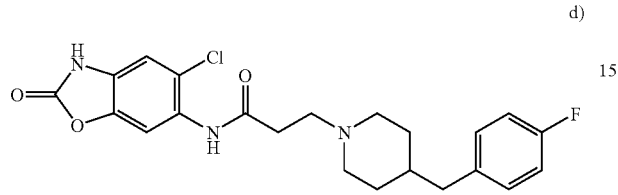

5-chloro-6-[3-(4-(4-fluorobenzyl)-1-piperidyl)propionamido]-2,3-dihydrobenzoxazol-2-one e)

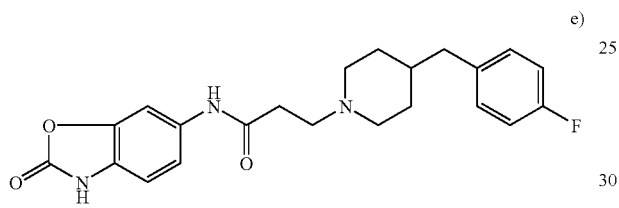

3-[4-(4-fluorobenzyl)-1-piperidyl]-N-(2-oxo-2,3-dihydrobenzoxazol-6-yl)propionamide f)

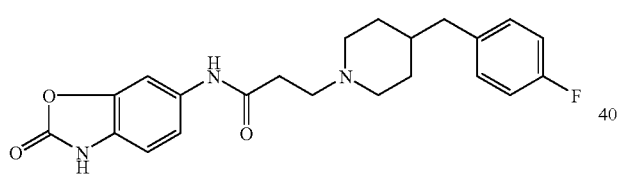

N-(2,3-dihydro-2-oxo-6-benzoxazolyl)-3-[4-(4-fluorobenzyl)-1-piperidyl]propionamide and pharmaceutically usable derivatives, solvates and stereoisomers thereof, including mixtures thereof in all ratios, and in particular salts and solvates thereof.

Furthermore preferred compounds of the formula I are compounds of the formula Ic

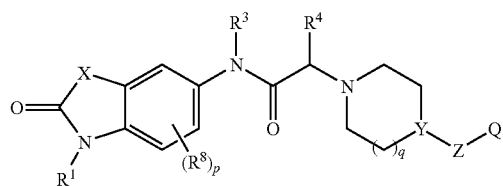

Ic in which

Q is as defined above and below and in which $R^1$ is H or A

A is straight-chain or branched alkyl having from 1 to 10 carbon atoms, alkenyl having from 2 to 10 carbon atoms, alkoxy having from 1 to 10 carbon atoms or alkoxyalkyl having from 2 to 10 carbon atoms, X is O, S, N—$R^2$, $CH_2$ or $CH_2CH_2$, $R^2$ is H or A $R^3$ is H, A, $(CH_2)_n$Het, $(CH_2)_n$Ar or cycloalkyl having from 3 to 7 carbon atoms, $R^4$ is H, A, cycloalkyl having from 3 to 7 carbon atoms, $(CH_2)_n$Het, $(CH_2)_n$Ar, $(CH_2)_n COR^6$, $(CH_2)_n CO(CH_2)_m$Ar, $(CH_2)_n CO(CH_2)_m$Het, $(CH_2)_n COO(CH_2)_m$Ar, $(CH_2)_n COO(CH_2)_m$Het, $(CH_2)_n OR^6$, $(CH_2)_n O(CH_2)_m$Ar $(CH_2)_n O(CH_2)_m$Het, $(CH_2)_n SR^6$, $(CH_2)_n S(CH_2)_m$Ar, $(CH_2)_n S(CH_2)_m$Het, $(CH_2)_n N(R^6)(CH_2)_m$Ar, $(CH_2)_n N(R^6)(CH_2)_m$Het, $(CH_2)_n SO_2N(R^6)(CH_2)_m$Ar, $(CH_2)_n N(R^6)SO_2(CH_2)_m$Ar, $(CH_2)_n SO_2N(R^6)(CH_2)_m$Het, $(CH_2)_n N(R^6)SO_2(CH_2)_m$Het, $(CH_2)_n CON(R^6)(CH_2)_m$Ar, $(CH_2)_n N(R^6)CO(CH_2)_m$Ar, $(CH_2)_n CON(R^6)(CH_2)_m$Het, $(CH_2)_n N(R^6)CO(CH_2)_m$Het, $(CH_2)_n N(R^6)_2$, CH=N—OA, $CH_2CH$=N—OA, $(CH_2)_n$NHOA, $(CH_2)_n(R^6)$Het, $(CH_2)_n$CH=N-Het, $(CH_2)_n OCOR^6$, $(CH_2)_n OC(O)N(R^6)_2$, $(CH_2)_n OC(O)NR^6(CH_2)_m$Ar, $(CH_2)_n OC(O)NR^6(CH_2)_m$Het, $(CH_2)_n NR^6COOR^6$, $(CH_2)_n NR^6COO(CH_2)_m$Ar, $(CH_2)_n NR^6COO(CH_2)_m$Het, $(CH_2)_n N(R^6)CH_2CH_2OR^6$, $(CH_2)_n N(R^6)CH_2CH_2OCF_3$, $(CH_2)_n N(R^6)C(R^6)HCOOR^6$, $(CH_2)_n N(R^6)CH_2COHet$, $(CH_2)_n N(R^6)CH_2Het$, $(CH_2)_n N(R^6)CH_2CH_2N(R^6)CH_2COOR^6$, $(CH_2)_n N(R^6)CH_2CH_2N(R^6)_2$, CH=CHCOOR^6, CH=CHCH_2NR^6Het, CH=CHCH_2N(R^6)_2, CH=CHCH_2OR^6, $(CH_2)_n N(COOR^6)COOR^6$, $(CH_2)_n N(CONH_2)COOR^6$, $(CH_2)_n N(CONH_2)CONH_2$, $(CH_2)_n N(CH_2COOR^6)COOR^6$, $(CH_2)_n N(CH_2CONH_2)COOR^6$, $(CH_2)_n N(CH_2CONH_2)CONH_2$, $(CH_2)_n CHR^6COR^6$, $(CH_2)_n CHR^6COOR^6$ or $(CH_2)_n CHR^6CH_2OR^6$, $(CH_2)_n OCN$, $(CH_2)_n NCO$, $R^6$ is H, A or cycloalkyl having from 3 to 7 carbon atoms, Y is CH, $COR^7$, $CSR^7$, or N, Z is O, S, N—$R^{15}$, $CH_2$ or $CH_2CH_2$, $R^{15}$ is H, A, $(CH_2)_n$Het, $(CH_2)_n$Ar or cycloalkyl having from 3 to 7 carbon atoms, Het is a saturated, unsaturated or aromatic mono- or bicyclic heterocyclic radical which is unsubstituted or mono- or polysubstituted by A, Hal, $NO_2$, CN, $OR^6$, $N(R^6)_2$, $COOR^6$, $CON(R^6)_2$, $NR^6COR^6$, $NR^6CON(R^6)_2$, $NR^6SO_2A$, $COR^6$, $SO_2NR^6$, $S(O)_wA$ and/or $OOCR^6$, Ar is an aromatic hydrocarbon radical having from 6 to 14 carbon atoms which is unsubstituted or mono- or polysubstituted by A, Hal, $NO_2$, CN, $OR^6$, $N(R^6)_2$, $COOR^6$, $CON(R^6)_2$, $NR^6COR^6$, $NR^6CON(R^6)_2$, $NR^6SO_2A$, $COR^6$, $SO_2NR^6$, $S(O)_wA$ and/or $OOCR^6$, n, m, independently of one another, are 0, 1, 2, 3, 4 or 5 p, q, independently of one another, are 0, 1, 2 or 3 r is 0, 1, 2, 3, 4 or 5, w is 0, 1, 2 or 3 and

Hal is F, Cl, Br or I, and $R^8$ independently is selected from the meanings of $R^4$ other than H or, independently of one another, is Hal, CN, $NO_2$, $OR^6$, $N(R^6)_2$, $COOR^6$, $CON(R^6)_2$, $NR^6COR^6$, $NR^6CON(R^6)_2$, $NR^6SO_2A$, $COR^6$, $SO_2NR^6$, $S(O)_wA$, $OOCR^6$ and/or C(NH)NOH, and pharmaceutically usable derivatives, solvates and stereoisomers thereof, including mixtures thereof in all ratios, and in particular salts and solvates thereof.

Furthermore preferred compounds of the formula I are compounds of the formula Id Id in which
R¹, X, R³, R⁴, Y, Z, R⁸, p and q are as defined above and below,
and in which
r 0, 1, 2, 3, 4 or 5, and the radicals
$R^9$ are selected, independently of one another, from the meanings of $R^4$ other than H or, independently of one another, are Hal, CN, NO₂, OR⁶, N(R⁶)₂, COOR⁶, CON(R⁶)₂, NR⁶COR⁶, NR⁶CON(R⁶)₂, NR⁶SO₂A, COR⁶, SO₂NR⁶, S(O)$_w$A, OOCR⁶ and/or C(NH)NOH, and pharmaceutically usable derivatives, solvates and stereoisomers thereof, including mixtures thereof in all ratios, and in particular salts and solvates thereof.

The present invention preferably relates to compounds of the formula I as described above in which $R^1$, $R^2$, r, Ar and Het are as defined above, and in which A is straight-chain alkyl having from 1 to 4 carbon atoms or branched alkyl having from 3 to 6 carbon atoms,
X is O or N—R²,
R³ is H or A,
R⁴ is H, A, (CH₂)$_n$Het, (CH₂)$_n$Ar, (CH₂)$_n$COO(CH₂)$_m$Ar, (CH₂)$_n$COO(CH₂)$_m$Het, (CH₂)$_n$OR⁶, (CH₂)$_n$O(CH₂)$_m$Ar, (CH₂)$_n$O(CH₂)$_m$Het, (CH₂)$_n$N(R⁶)(CH₂)$_m$Ar, (CH₂)$_n$ N(R⁶)(CH₂)$_m$Het, (CH₂)$_n$SO₂N(R⁶)(CH₂)$_m$Ar, (CH₂)$_n$ N(R⁶)SO₂(CH₂)$_m$Ar, (CH₂)$_n$SO₂N(R⁶)(CH₂)$_m$Het, (CH₂)$_n$N(R⁶)SO₂(CH₂)$_m$Het, (CH₂)$_n$N(R⁶)₂, (CH₂)$_n$ HOA, (CH₂)$_n$(R⁶)Het, (CH₂)$_n$OCOR⁶, (CH₂)$_n$ OC(O)N(R⁶)₂, (CH₂)$_n$OC(O)NR⁶(CH₂)$_m$Ar, (CH₂)$_n$ OC(O)NR⁶(CH₂)$_m$Het, (CH₂)$_n$NR⁶COOR⁶, (CH₂)$_n$ NR⁶COO(CH₂)$_m$Ar, (CH₂)$_n$NR⁶COO(CH₂)$_m$Het,
R⁶ is H or A,
Y is CH, COR⁷ or N,
R⁷ is H, A, (CH₂)$_n$Het or (CH₂)$_n$Ar,
Z is O, CH₂ or CH₂CH₂,
n, m, independently of one another, are 0, 1, 2 or 3, and
p, q, independently of one another, are 0, 1 or 2, and
R⁸, R⁹ are selected, independently of one another, from the meanings of $R^4$ other than H or, independently of one another, are F, Cl, Br, I, CN, NO₂, NH₂, CF₃, OCF₃, C(NH)NOH and SO₂CH₃,
and solvates and salts thereof.

The sum of n and m is preferably greater than zero.

Some preferred groups of compounds can be expressed by the following sub-formulae Iη) to Iμ), which conform to the formula I, preferably to the formula Ic and particularly preferably to the formula Id and in which the radicals not designated in greater detail are as defined above, but in which
in Iη) R¹ is H;
in Iθ) R¹ is H and
X is O, S or NR²;
in Iι) R¹ is H,
X is O, S or NR²,
R² is H, R³ is H or A, and
R⁹ is Hal;
in Iκ) R¹ is H,
X is O, S or NR²,
R² is H,
R³ is H or A,
Y is CH, COR⁶ or N, and
R⁹ is Hal;
in Iλ) R¹ is H,
X is O, S or NR²,
R² is H,
R³ is H or A,
Y is CH, COR⁶ or N,
R⁶ is H,
Z is O, CH₂, CH₂CH₂ or N—R¹⁵,
R¹⁵ is H or A, and
R⁹ is Hal;
in Iμ) R¹ is H,
X is O, S or NR²,
R² is H,
R³ is H or A,
R⁴ is H or A,
Y is CH, COR⁶ or N,
R⁶ is H,
Z is O, CH₂, CH₂CH₂ or N—R¹⁵,
R¹⁵ is H or A, and
R⁹ is Hal.

In a preferred embodiment of the present invention, the radical $R^8$ in the sub-formulae Iη) to Iμ) is A, Hal, in particular F or Br, CN, NO₂ NH₂, CF₃, OCF₃ or SO₂CH₃, particularly preferably A or Hal; p is 0, 1 or 2, particularly preferably 0 or 1; q is 0, 1 or 2, particularly preferably 1 or 2; and r is 0, 1, 2 or 3, particularly preferably 0, 1 or 2. In this preferred embodiment, the radical $R^9$ in the sub-formulae Iη) to Iλ) is particularly preferably A, F, Cl, Br, I, CN, NO₂, NH₂, CF₃, OCF₃ or SO₂CH₃ and in particular F. In this preferred embodiment, the radical $R^4$ in the sub-formulae Iη) to Iμ) is preferably H, methyl, ethyl, trifluoromethyl, pentafluoroethyl, propyl, isopropyl, butyl, isobutyl, sec-butyl, tert-butyl or phenyl, particularly preferably H, methyl, ethyl, trifluoromethyl, phenyl and in particular H, methyl or phenyl.

In a specific and preferred embodiment, the present invention relates to a compound of the formula I in which X is O, and solvates and salts thereof.

In a further specific and preferred embodiment, the present invention relates to a compound of the sub-formulae Iη) to Iμ) as defined above in which X is O, and solvates and salts thereof.

In a further specific and preferred embodiment, the present invention relates to a compound of the formula I, of the formula Ic, of the formula Id and of the sub-formulae Iη) to Iμ) as defined above in which $R^4$ is selected from H, substituted or unsubstituted alkyl radicals, preferably unsubstituted alkyl radicals, in particular alkyl radicals having from one to four carbon atoms, and substituted or unsubstituted aryl radicals, preferably unsubstituted aryl radicals, unsubstituted phenyl radicals, and solvates and salts thereof. $R^4$ is particularly preferably selected from H, methyl and phenyl.

In a further specific and particularly preferred embodiment, the present invention relates to a compound of the formula I, of the formula Ic, of the formula Id and in particular one of the sub-formulae Iη) to Iμ) as defined above and solvates and salts thereof in which X is O and in which the radical $R^8$ is A, Hal, in particular F or Br, CN, NO₂ NH₂, CF₃, OCF₃ or SO₂CH₃, particularly preferably A or Hal; p is 0, 1 or 2, particularly preferably 0 or 1; q is 0, 1 or 2, particularly preferably 1 or 2; and r is 0, 1, 2 or 3, particularly preferably 0, 1 or 2. In this specific and particularly preferred embodiment, the radical $R^9$ in the sub-formulae Iη) to Iλ) is particularly preferably A, F, Cl, Br, I, CN, $NO_2$, $NH_2$, $CF_3$, $OCF_3$ or $SO_2CH_3$ and in particular F. Furthermore in this further specific and particularly preferred embodiment, the radical $R^4$ in the sub-formulae Iη) to Iλ) is preferably H, methyl, ethyl, trifluoromethyl, pentafluoroethyl, propyl, isopropyl, butyl, isobutyl, sec-butyl or tert-butyl, particularly preferably H, methyl, ethyl, trifluoromethyl, pentafluoroethyl or phenyl and in particular H, methyl or phenyl. Preferably in this further specific and particularly preferred embodiment, the radical $R^4$ in the sub-formulae Iη) to Iλ) is preferably H, methyl, ethyl, trifluoromethyl, pentafluoroethyl, propyl, isopropyl, butyl, isobutyl, sec-butyl or tert-butyl, particularly preferably H, methyl, ethyl, trifluoromethyl, pentafluoroethyl and in particular H or methyl.

In a further very particularly preferred embodiment of the present invention, the compounds of the formula I are selected from g) 2-[4-(4-fluorobenzyl)4-hydroxypiperidin-1-yl]-N-(2-oxo-2,3-dihydrobenzooxazol-6-yl)acetamide;
h) 2-[4-(4-fluorophenoxy)piperidin-1-yl]-N-(2-oxo-2,3-dihydrobenzooxazol-6-yl)propionamide;
i) 2-[4-(4-fluorobenzyl)piperidin-1-yl]-N-(2-oxo-2,3-dihydrobenzooxazol-6-yl)propionamide;
j) 2-(4-benzylpiperazin-1-yl)-N-(2-oxo-2,3-dihydrobenzooxazol-6-yl)propionamide;
k) 2-[4-(4-fluorobenzyl)-4-hydroxypiperidin-1-yl]-N-(2-oxo-2,3-dihydrobenzoxazol-6-yl)propionamide;
l) 2-[4-(3,5-difluorobenzyl)-4-hydroxypiperidin-1-yl]-N-(2-oxo-2,3-dihydrobenzoxazol-6-yl)propionamide
m) 6-(2-(4-(4-fluorobenzyl)-1-piperidyl)acetamido)-2,3-dihydrobenzoxazol-2-one
n) 2-[4-(4-fluorobenzyl)piperidin-1-yl]-N-(2-oxo-2,3-dihydrobenzooxazol-6-yl)-2-phenylacetamide
o) 2-[4-(4-fluorophenoxy)piperidin-1-yl]-N-(2-oxo-2,3-dihydrobenzooxazol-6-yl)-2-phenylacetamide
p) 2-[4-(2,4-difluorobenzyl)piperidin-1-yl]-N-(2-oxo-2,3-dihydrobenzooxazol-6-yl)propionamide
q) 2-(4-benzyl-1-piperidyl)-N-(2-oxo-2,3-dihydrobenzoxazol-6-yl)acetamide
r) N-(2-oxo-2,3-dihydrobenzoxazol-6-yl)-2-(4-thiophen-2-ylmethyl-1-piperidyl)acetamide and pharmaceutically usable derivatives, solvates and stereoisomers thereof, including mixtures thereof in all ratios, and in particular salts and solvates thereof.

Furthermore preferred compounds of the formula I are compounds of the formula Ie

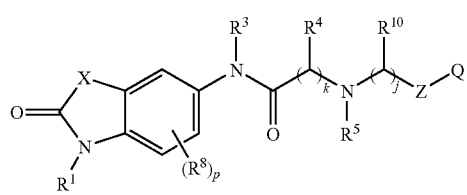

in which
X, $R^1$, $R^3$, $R^4$, k, Z and Q are as defined above and below
and in which
$R^5$ is H, A, $(CH_2)_n$Het, $(CH_2)_n$Ar or cycloalkyl having from 3 to 7 carbon atoms,
$R^{10}$ independently is H, A, $(CH_2)_n$Het, $(CH_2)_n$Ar or cycloalkyl having from 3 to 7 carbon atoms, and
j is 1, 2, 3 or 4 and in particular 2 or 3, and pharmaceutically usable derivatives, solvates and stereoisomers thereof, including mixtures thereof in all ratios, and in particular salts and solvates thereof.

Preferred compounds of the formula Ie are compounds of the formula If

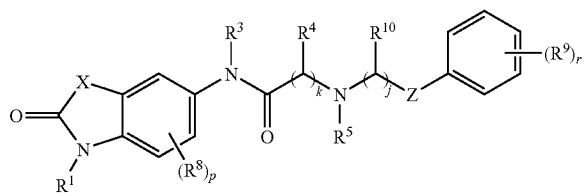

in which
X, $R^1$, $R^3$, $R^4$, k, Z, $R^5$, $R^{10}$ and j are as defined above and below and in which
r is 0, 1, 2, 3, 4 or 5, preferably 0, 1, 2 or 3 and in particular 0, 1, 2 or 3, and
$R^9$ independently is selected from the meanings of $R^4$ other than H or, independently of one another, is Hal, CN, $NO_2$, OR, $N(R^6)_2$, $COOR^6$, $CON(R^6)_2$, $NR^6COR^6$, $NR^6CON(R^6)_2$, $NR^6SO_2A$, $COR^6$, $SO_2NR^6$, $S(O)_wA$, $OOCR^6$ and/or C(NH)NOH, and the pharmaceutically usable derivatives, solvates and stereoisomers thereof, including mixtures thereof in all ratios, and in particular salts and solvates thereof.

The present invention preferably relates to compounds of the formula I and in particular compounds of the formula If as described above in which A is straight-chain alkyl having from 1 to 4 carbon atoms, branched alkyl having from 3 to 6 carbon atoms, alkoxy having from 1 to 4 carbon atoms, X is O or N—$R^2$, and $R^3$ is H or A, $R^4$ are selected, independently of one another, from H, A, $(CH_2)_n$Het, $(CH_2)_n$Ar, $(CH_2)_n$COO$(CH_2)_m$Ar, $(CH_2)_n$COO$(CH_2)_m$Het, $(CH_2)_n$OR$^6$, $(CH_2)_n$O$(CH_2)_m$Ar, $(CH_2)_n$O$(CH_2)_m$Het, $(CH_2)_n$N$(R^6)$$(CH_2)_m$Ar, $(CH_2)_n$N$(R^6)$$(CH_2)_m$Het, $(CH_2)_n$SO$_2$N$(R^6)$$(CH_2)_m$Ar, $(CH_2)_n$N$(R^6)$SO$_2$$(CH_2)_m$Ar, $(CH_2)_n$SO$_2$N$(R^6)$$(CH_2)_m$Het, $(CH_2)_n$N$(R^6)$SO$_2$$(CH_2)_m$Het, $(CH_2)_n$N$(R^6)_2$, $(CH_2)_n$NHOA, $(CH_2)_n$$(R^6)$Het, $(CH_2)_n$OCOR$^6$, $(CH_2)_n$OC(O)N$(R^6)_2$, $(CH_2)_n$OC(O)NR$^6$$(CH_2)_m$Ar, $(CH_2)_n$OC(O)NR$^6$$(CH_2)_m$Het, $(CH_2)_n$NR$^6$COOR$^6$, $(CH_2)_n$NR$^6$COO$(CH_2)_m$Ar, $(CH_2)_n$NR$^6$COO$(CH_2)_m$Het, and $R^6$ is H or A, $R^5$ is H or A, preferably H or alkyl, in particular H or methyl, Z is O, $CH_2$ or $CH_2CH_2$, in particular $CH_2$, n, m, independently of one another, are 0, 1, 2 or 3, p is 0, 1 or 2, preferably 0 or 1, particularly preferably 0, k is 1 or 2, preferably 1, j is 2 or 3, preferably 3, and r is 0, 1 or 2, preferably 1, and $R^9$ independently is selected from the meanings of $R^4$ other than H or independently is F, Cl, Br, 1, CN, $NO_2$, $NH_2$, $CF_3$, $OCF_3$, C(NH)NOH and $SO_2CH_3$ and in particular F.

and solvates and salts thereof,

The sum of n and m is preferably greater than zero.

Preferred compounds of the formula Ie or If are compounds of the formula Ig

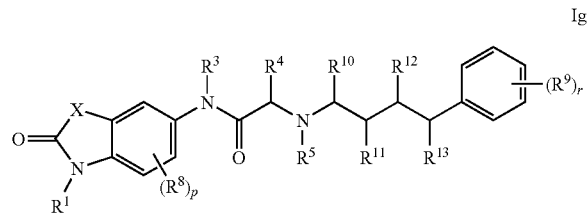

in which
R¹, R³ are H or methyl, preferably H,
R⁴ is H or or A, preferably H,
R⁵ is H or or A, preferably H or methyl,
and R¹⁰, R¹¹ and R¹², R¹³ independently of one another, are Ar, H or A, preferably H or A, and in particular are H.

Particularly preferred compounds of the formulae Ie to Ig are selected from

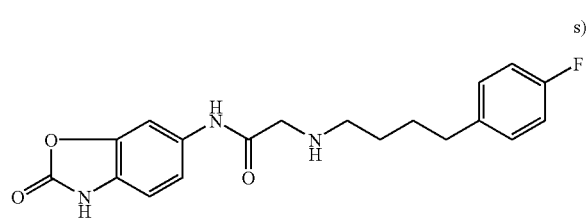

N-(2,3-dihydro-2-oxobenzoxazol-6-yl)-2-[4-(4-fluorophenyl)butylamino]-acetamide

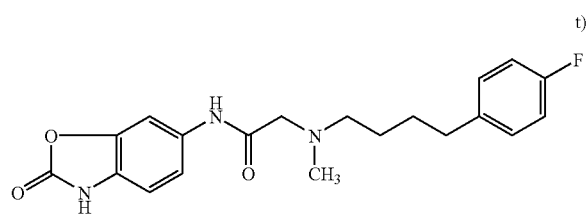

N-(2,3-dihydrobenzoxazol-6-yl)-2{N-[4-(4-fluorophenyl)butyl]-N-methylamino}acetamide, and pharmaceutically usable derivatives, solvates and stereoisomers thereof, including mixtures thereof in all ratios, and in particular salts and solvates thereof.

Depending on the choice of the substituents and radicals described above, the compounds according to the invention can have one or more chiral centres, in particular one or more chiral carbon atoms. If a compound of defined composition according to the invention has one or more chiral centres, this compound of defined composition can be in the form of various stereoisomers. The present invention relates to all possible such stereoisomers of compounds according to the invention, which can exist either as individual, stereochemically uniform compounds or as mixtures of two or more stereochemically uniform compounds. In the case of mixtures of two or more stereoisomers, the individual stereoisomers may be present in different or identical proportions. In mixtures of two stereoisomers present him identical proportions and represent optical antipodes, the term racemic mixtures is used. Racemic mixtures of compounds of the formula I are likewise a subject-matter of the present invention.

The present invention relates, in particular, to stereoisomers formed through the fact that the radical R⁴ or one radical R⁴ or both radicals R⁴ has a meaning other than H.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart;), to be precise under reaction conditions which are known and suitable for the said reactions. Use can also be made here of variants which are known per se, but are not mentioned here in greater detail.

The starting materials, for example the compounds of the formula II, V and/or VI, can, if desired, also be formed in situ by not isolating them from the reaction mixture, but instead immediately converting them further into the compound of the formula I.

The compounds of the formula I can preferably be obtained by reacting compounds of the formula II with compounds of the formula V and of the formula VI. The sequence of reaction of the compounds here is in principle immaterial. For example, the compounds of the formula II, V and VI can be converted into compounds of the formula I in a one-pot reaction. Depending on the choice of groups L¹, L², L³ and L⁴, however, a certain sequence in the reaction of the starting compounds may be advantageous. In many cases, it is advantageous first to react the starting compound of the formula II with a starting compound of the formula V, and subsequently to react the resultant reaction product with a starting compound of the formula VI to give a compound of the formula I (the reaction in this sequence is referred to below as variant 1). Alternatively, a starting compound of the formula V can firstly be reacted with a starting compound of the formula VI, and the resultant product of this reaction reacted with a starting compound of the formula II to give a compound of the formula I (the reaction in this sequence is referred to below as variant 2).

In the compounds of the formula II, L¹ is preferably H or a group which activates the amino function, for example a metal ion. Suitable metal ions are, in particular, alkali metal, alkaline earth metal or aluminium ions.

Preferred metal ions are alkali metal ions, in particular Li, Na or K. In the case of polyvalent metal ions, a complex of metal ion and two or more compounds of the formula II frequently forms, where in general the complex stoichiometrically includes as many compounds of the formula II as corresponds to the valency of the metal ion.

In the compounds of the formula V, L² is preferably Cl, Br, I, OH or a reactively modified OH group, such as alkylsulfonyloxy having 1-6 carbon atoms (preferably methylsulfonyloxy or trifluoromethylsulfoxy or trifluoromethanesulfonyloxy) or arylsulfonyloxy having 6-10 carbon atoms (preferably phenyl- or p-tolylsulfonyloxy).

In the compounds of the formula V, L³ is preferably Cl, Br, I, OH or a leaving group which activates this carbon atom, for example a diazonium group.

In the compounds of the formula VI, L⁴ is preferably H or a group which activates the amino function, for example a metal ion. Suitable metal ions are, in particular, alkali metal, alkaline earth metal or aluminium ions. Preferred metal ions are alkali metal ions, in particular Li, Na or K. In the case of polyvalent metal ions, the compounds of the formula VI generally exhibit a similar behaviour as described above in the case of the compounds of the formula II.

The reaction in variant 1 is particularly advantageous if the groups $L^2$ and/or $L^3$, preferably $L^2$ and $L^3$, in the starting compound V are halogen, in particular Cl, and the group $L^1$ in the starting compound II is preferably H and/or the group $L^4$ in the starting compound VI is H. In variant 1, the groups $L^2$ and $L^3$ are particularly preferably halogen, in particular Cl, and the groups $L^1$ and $L^4$ are particularly preferably H.

The starting compounds of the formulae II and VI are generally novel. However, they can be prepared by methods known per se. The starting compounds of the formula V are either novel or known from the literature or commercially available. In any case, however, they can be prepared by methods known per se.

The reaction of the compounds of the formula II with compounds of the formula V is generally carried out in an inert solvent, preferably in the presence of an acid-binding agent. Suitable acid-binding agents are all bases which are usual in synthetic organic chemistry, both inorganic and organic bases, preferably organic bases. Examples of suitable organic bases are triethylamine, diisopropylamine, diisopropylethylamine (DIPEA), dimethylaniline, pyridine or quinoline. The addition of an inorganic base, such as, for example, an alkali or alkaline earth metal hydroxide, carbonate or bicarbonate, or another salt of a weak acid of the alkali or alkaline earth metals, preferably of potassium, sodium, calcium or caesium, may also be favourable.

The reaction time is, depending on the conditions used, between a few minutes and 14 days, and the reaction temperature is between about −30° and 180°, normally between −20° and 140°, preferably between −10° and 130° and in particular between about 0° and about 120°. In many cases, it is favourable to carry out the reaction of a starting compound of the formula II with a starting compound of the formula V at comparatively low temperatures, for example at a temperature in the range from −20 to 100, preferably from 0° to 80° and in particular from 0° to 50, for example approximately at room temperature (20°). In the case of a reaction in this temperature range, it is in many cases favourable to use an organic base, such as triethylamine or diisopropylamine. In many cases, it is favourable to carry out the reaction product obtained on reaction of compounds of the formula II with compounds of the formula V at at comparatively low temperatures, for example at a temperature in the range from −20° to 100°, preferably from 0° to 80° and in particular from 0° to 50°, for example approximately at room temperature (20°). In the case of a reaction in this temperature range, it is in many cases favourable to use an organic base, such as triethylamine, diisopropylethylamine or diisopropylamine. In many cases, it is favourable to react the reaction product obtained on reaction of compounds of the formula II with compounds of the formula V with a starting compound of the formula VI at elevated temperatures. Suitable elevated temperatures are, for example, in the range from 20° to 170°, preferably from 60° to 150° and in particular from 80° to 130°, for example at about 120°. In the case of a reaction in this temperature range, it is in many cases favourable to employ an organic base, such as pyridine or quinoline, which only boils at elevated temperatures.

Suitable inert solvents are, for example, hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, water, or mixtures of the said solvents.

A reaction of a compound of the formula II with a compound of the formula V can advantageously be carried out at comparatively low temperatures in a low-boiling inert solvent, for example hydrocarbons, such as petroleum ether or hexane, or chlorinated hydrocarbons, such as chloroform or dichloromethane.

A reaction of the product of the reaction of a compound of the formula II and a compound of the formula V with a compound of the formula VI can advantageously be carried out at comparatively low temperatures in a polar inert solvent, for example chlorinated hydrocarbons, such as dichloromethane and chloroform, dimethylformamide (DMF), acetonitrile, sulfoxides, such as dimethyl sulfoxide (DMSO), and in particular in acetonitrile.

A reaction of the product of the reaction of a compound of the formula II and a compound of the formula V with a compound of the formula VI at elevated temperatures can advantageously be carried out in a relatively high-boiling inert solvent, for example hydrocarbons, such as benzene, toluene or xylene, chlorinated hydrocarbons, such as trichloroethylene or 1,2-dichloroethane, glycol ethers, such as ethylene glycol monomethyl or monoethyl ether or ethylene glycol dimethyl ether (diglyme), and dimethylformamide (DMF), acetonitrile, sulfoxides, such as dimethyl sulfoxide (DMSO), or nitro compounds, such as nitromethane or nitrobenzene. The reaction at elevated temperatures can advantageously be carried out in a relatively high-boiling organic base, such as pyridine or quinoline, instead of a solvent.

In many cases, the reaction of the starting compounds of the formula II, the formula V and/or of the formula VI or the reaction of the product of the reaction of a compound of the formula II and a compound of the formula V with a compound of the formula VI or the reaction of the product of the reaction of a compound of the formula V with a compound of the formula VI with a compound of the formula II can advantageously be carried out in at least one organic base, preferably at least one of the organic bases mentioned above, instead of a solvent.

The invention also relates to the optically active forms (stereoisomers), the enantiomers, the racemates, the diastereomers and the hydrates and solvates of the compounds according to the invention. The term solvates of the compounds is taken to mean adductions of inert solvent molecules onto the compounds which form owing to their mutual attractive force. Solvates are, for example, monohydrates or dihydrates or alcoholates.

The term pharmaceutically usable derivatives is taken to mean, for example, the salts of the compounds according to the invention and also so-called prodrug compounds according to the invention.

The term prodrug derivatives is taken to mean compounds of the formula I which have been modified with, for example, alkyl or acyl groups, sugars or oligopeptides and which are rapidly cleaved in the organism to give the effective compounds according to the invention.

These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclc monobasic or polybasic carboxylic, sulfonic or sulfuric acids, for example formic acid, acetic acid, trichloroacetic acid, trifluoroacetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate). It is also possible to use physiologically acceptable organic bases, such as, for example, ethanolamine.

The compounds according to the invention can be used as therapeutic agents, diagnostic agents and/or cosmetics or together with one or more active ingredients other than the compounds according to the invention and/or adjuvants in therapeutic agents, diagnostic agents and/or cosmetics. The compounds according to the invention are usually employed in the form of pharmaceutical, diagnostic and/or cosmetic formulations. Formulations of this type and processes for the preparation thereof are known to the person skilled in the art.

Examples of formulations of this type are suspensions, emulsions, solutions, liposomes, salts, pastes, biodegradable polymers, nanoparticles, tablets, coated tablets, sugar-coated tablets, film-coated tablets, capsules, pills, granules, powders, aerosols, drops or sprays comprising at least one compound according to the invention.

The compounds according to the invention or formulations which comprise at least one compound according to the invention can be administered to humans or animals, for example locally or systemically and in particular orally, intravenously, intraperitoneally, subcutaneously, transdermally, nasally, buccally and/or iontophoretically.

The invention furthermore relates to the use of the compounds of the formula I and/or physiologically acceptable salts thereof for the preparation of pharmaceutical compositions, in particular by non-chemical methods. They can be converted here into a suitable dosage form together with at least one solid, liquid and/or semi-liquid excipient or adjuvant and, if desired, in combination with one or more further active ingredients.

The invention furthermore relates to pharmaceutical compositions comprising an effective amount of at least one of the compounds of the formula I and/or a physiologically acceptable salt thereof.

These compositions can be used as medicaments in human or veterinary medicine. Suitable excipients are organic or inorganic substances which are suitable for enteral (for example oral), parenteral or topical administration or administration in the form of an inhalation spray and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or Vaseline. Suitable for oral administration are, in particular, tablets, pills, sugar-coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders. The novel compounds may also be lyophilised and the resultant lyophilisates used, for example, to prepare injection preparations. The compositions indicated may be sterilised and/or comprise adjuvants, such as lubricants, preservatives, stabilisers and/or wetting agents, emulsifying agents, salts for modifying the osmotic pressure, buffer substances, colorants and flavours and/or a plurality of further active ingredients, for example one or more vitamins.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronised form, in which case one or more additional physiologically tolerated solvents may be present, for example ethanol. Inhalation solutions can be administered with the aid of conventional inhalers.

The present invention therefore relates to a process for the preparation of pharmaceutical compositions which is characterised in that a compound of the formula I according to claim 1 and/or a physiologically acceptable salt thereof and/or a solvate thereof is converted into a suitable dosage form together with at least one solid, liquid or semi-liquid excipient or adjuvant.

The compounds of the formula I and/or physiologically acceptable salts thereof can be used as excitatory amino acid antagonist for combating diseases, in particular for combating neurodegenerative diseases, including cerebrovascular diseases, epilepsy, schizophrenia, Alzheimer's disease, Parkinson's disease, Huntington's disease, cerebral ischaemia, infarction or psychoses.

The present compound therefore relates to the use of compounds of the formula I according to claim 1 and/or physiologically acceptable salts or solvates thereof for the preparation of a medicament for the prophylaxis and/or treatment of schizophrenia, depression, dementia, Parkinson's disease, Alzheimer's disease, Lewy bodies dementia, Huntington's disease, Tourette's syndrome, anxiety, learning and memory impairment, neurodegenerative diseases and other cognitive impairments, as well as nicotine dependence and pain.

In general, the compounds according to the invention can be administered analogously to other known compounds having a similar action profile, such as, for example, ifenprodil, preferably in doses between about 0.05 and 500 mg, in particular between 0.5 and 100 mg, per dosage unit. The daily dose is preferably between about 0.01 and 2 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

The compounds according to the invention exhibit an advantageous action profile and are comparatively easy to prepare. Thus, the compounds according to the invention are preferably distinguished as polyamine antagonists having selective binding to the NR2B receptor of the NMDA subreceptor class having a preferably very slight QT extension for the treatment of the diseases as described above. Furthermore, in receptor binding tests, compounds according to the invention exhibit an affinity to the ifenprodil binding site of the NMDA receptor preferably even in nanomolar concentrations.

Above and below, all temperatures are given in ° C. In the following examples, "conventional work-up" means that water is added if necessary, the pH is adjusted, if necessary, to between 2 and 10, depending on the constitution of the end product, the mixture is extracted with ethyl acetate or dichloromethane, the phases are separated, if necessary the organic phase is dried, for example over sodium sulfate, the organic phase is evaporated, and the residue obtained is purified by chromatography, for example on silica gel, and/or by crystallisation. Unless stated otherwise, HPLC analyses are carried out on a 3μ Silica-Rod column with a 210-second gradient from 20% to 100% with water/acetonitrile/0.01% trifluoroacetic acid as eluent at a flow rate of 2.2 ml/min. The detection is carried out at a wavelength of 220 nm.

EXAMPLE 1

Synthesis of 3-[4-(fluorobenzyl)-1-piperidyl]-N-(2-oxo-2,3-dihydrobenzoxazol-6yl)propionamide

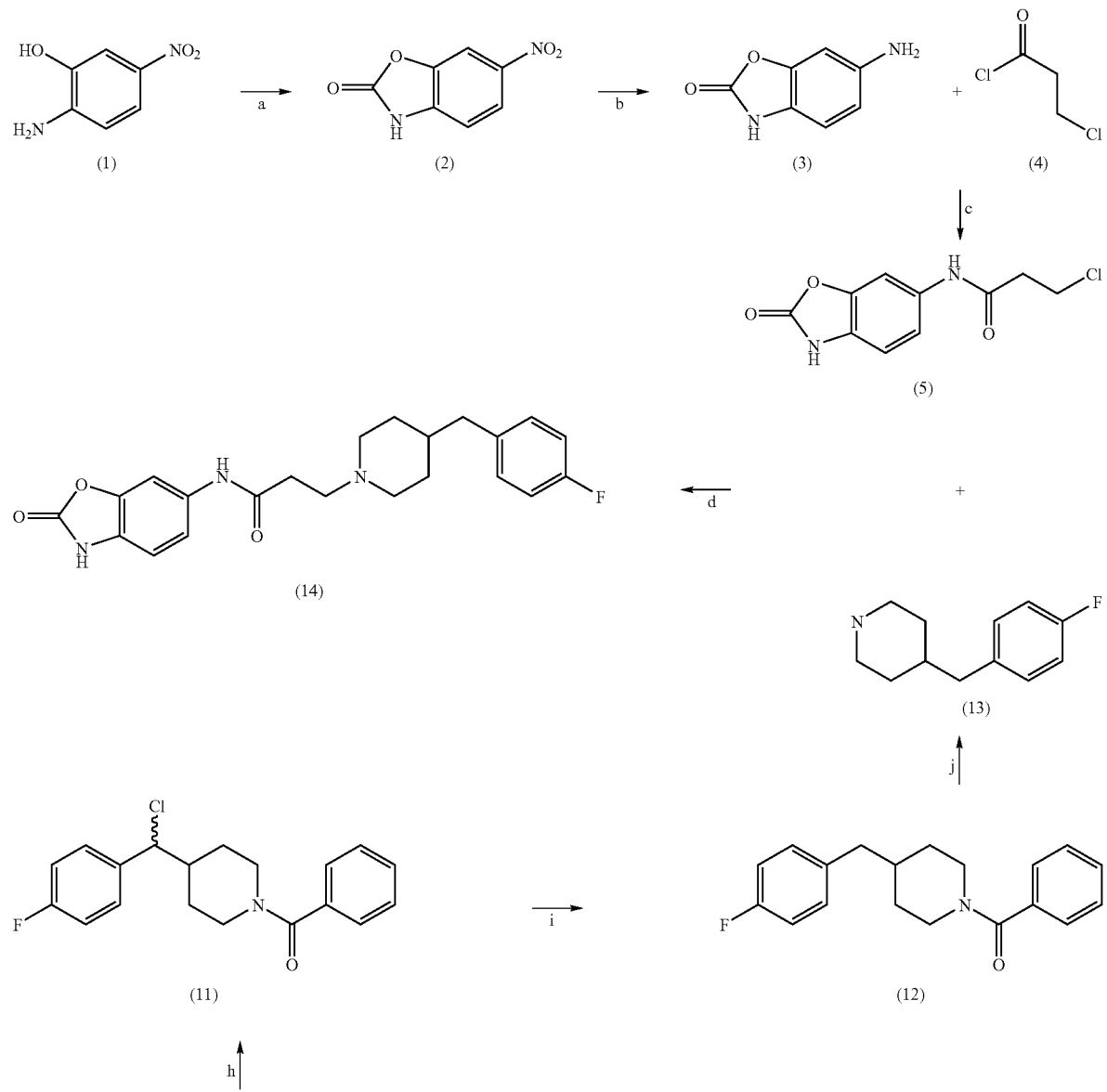

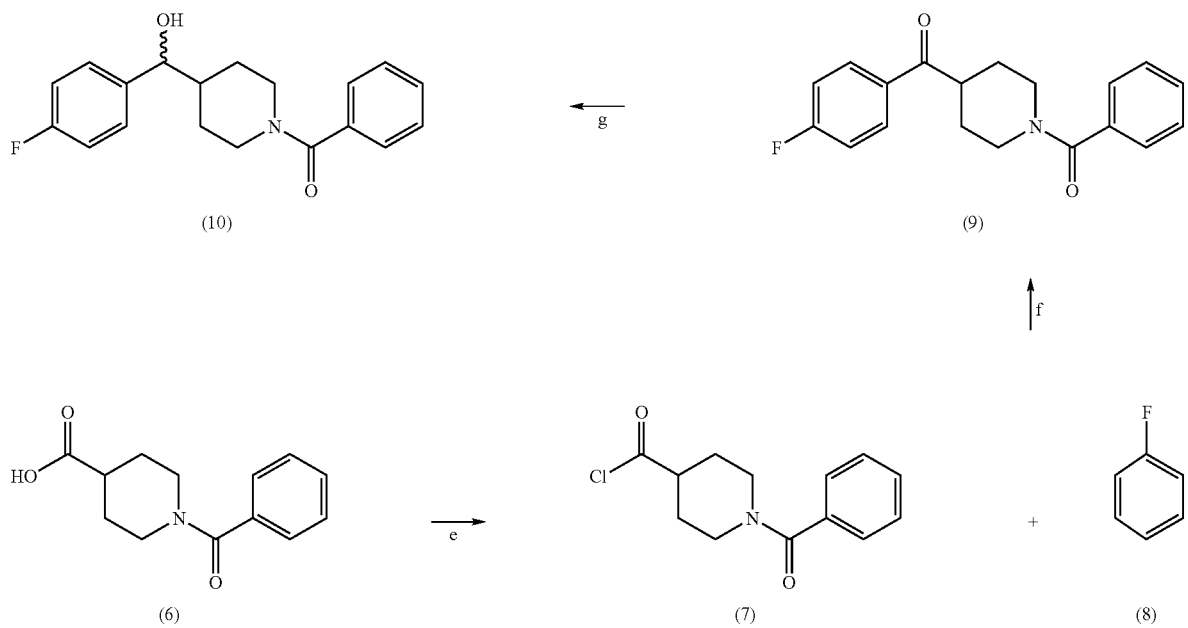

a) A solution of 30.83 g (0.2 mol) of 2-hydroxy-4-nitroaniline and 48.64 g (0.3 mol) of carbonyldiimidazole in 400 ml of dried THF is stirred under reflux for three hours. For work-up, the solvent is distilled off, the residue is treated with 300 ml of 1 N hydrochloric acid in an ultrasound bath for 30 minutes, and the precipitate is filtered off under reduced pressure, washed like 30 water and a little methanol and dried at 50° C. under reduced pressure. Yield: 33.3 g (92%); melting point: 246-249° C.

b) 22 g of 5 percent palladium/active carbon are added to a solution of 225 g of nitrobenzoxazolone (2) in 2.3 litres of methanol, and the mixture is hydrogenated overnight in a hydrogen atmosphere. The catalyst is subsequently filtered off, the filter cake is washed with a mixture of dichloromethane/methanol (9:1), and the filtrate is freed from solvent. The residue which remains is dissolved in hot methanol and cooled, and the crystalline solid formed is filtered under reduced pressure. The crystalline solid is washed with cold methanol and diethyl ether and dried at 50° C. under reduced pressure. Yield: 169 g (100%); melting point: 206-208° C.

c) 2.46 g (0.024 mol) of triethylamine are added with stirring to a suspension of 3.32 g (0.022 mol) of aminobenzoxazolidinone in 30 ml of dichloromethane. 3-Chloropropionyl chloride, dissolved in 10 ml of dichloromethane, is subsequently added to the reaction mixture with stirring and cooling at such a rate that the temperature does not exceed 20° C. When the addition is complete, the mixture is stirred with cooling for a further 24 hours. For work-up, the reaction mixture is filtered under reduced pressure, the crystalline residue obtained is stirred with water, filtered again under reduced pressure and dried. Yield: 1.27 g (24%); melting point: 237° C.

d) 1.10 gram (10.9 mmol) of triethylamine and 1.25 gram (5.4 mmol) of the 4-fluoro-4-benzylpiperidine (13) obtained in accordance with j) are added to a suspension of 1.19 g (4.9 mmol) of the alkyl chloride (5) obtained under step c) in 20 ml of acetonitrile, and the mixture is stirred at room temperature for 24 hours. The precipitate formed is filtered off, taken up in dichloromethane, washed with water, dried and evaporated to dryness in a rotary evaporator. The residue is triturated with a little diethyl ether, filtered under reduced pressure and dried at 50° C. under reduced pressure. Yield: 1.32 g (67%); melting point: 192-194° C.

e) 34.99 g (15 mmol) of benzoylpiperidine-4-carboxylic acid (6) are dissolved in 100 ml of dichloromethane in a 1 l three-necked flask provided with magnetic stirrer, condenser, dropping funnel and gas-discharge tube, and 16.32 ml of thionyl chloride are added with stirring. The reaction mixture is subsequently refluxed for two hours, cooled, freed from solvent in a rotary evaporator and stored in the refrigerator overnight. The product obtained in this way can be reacted further without further purification.

f) 42.5 ml of fluorobenzene are added dropwise to a suspension of 101 g of aluminium trichloride in 160 ml of dichloromethane with exclusion of moisture ($N_2$ atmosphere) and at room temperature without detectable evolution of heat. A solution of 78.0 g of benzoylpiperidine-4-carbonyl chloride (7) in 160 ml of dichloromethane is subsequently added dropwise at such a rate that the gas evolution does not take place too vigorously and the internal temperature does not exceed 35° C. (about 20 minutes), and the mixture is stirred at room temperature for a further 1.5 hours. For work-up, the reaction mixture is poured onto ice (about 1 kg) and extracted twice with 350 ml of dichloromethane, and the combined organic phases are washed successively with 1 N HCl (400 ml), semisaturated sodium hydrogencarbonate solution (400 ml, about 4 percent) and water (400 ml), dried using sodium sulfate and filtered under reduced pressure. The filter residue is washed with dichloromethane, and the solvent is distilled off. The residue obtained (107 g) was crystallised using 200 ml of methyl t-butyl ether. Yield: 270.6 g; melting point: 128-129° C.

g) 4.0 g of NaBH$_4$ are added in portions over about 30 minutes to a suspension of 93.3 g of the compound. (9) obtained in accordance with f) in 375 ml of methanol with ice/water cooling that the temperature does not exceed 13° C. When the addition is complete, the reaction mixture is stirred for about a further 30 minutes with cooling. 375 ml of ice/water are subsequently added, the mixture is stirred for 10 minutes and and extracted once with 300 ml and twice 100 ml of dichloromethane.

The combined organic phases are washed with 300 ml of water and dried using sodium sulfate. The solvent is subsequently removed under reduced pressure. The residue obtained is recrystallised from methyl t-butyl ether. Yield: 91.2 g; melting point 116-117.5° C.

h) 31 ml of SOCl$_2$ are added over the course of about 10 minutes to a solution of 88.3 g of the alcohol (10) obtained under g) in 425 ml of dichloromethane with exclusion of moisture at a temperature in the range 16-18° C., and the mixture is subsequently stirred at room temperature for a further hour. The solvent is subsequently removed under reduced pressure, the residue is dissolved in 175 ml of diethyl ether, and petroleum ether (b.p. 40-60° C.; about 35 ml) is added to the cloudiness threshold. When crystallisation is complete, the product is filtered off with suction and dried at 50° C. under reduced pressure. Yield: 89.7 g; melting point: 115.5-117° C.

i) 1.1 kg of palladium/active carbon (5%) are added to 2.1 kg of the compound (II) obtained in accordance with h), dissolved in 25 l of THF, and the mixture is hydrogenated overnight at room temperature with stirring at a pressure of 5 bar in a hydrogen atmosphere. The reaction mixture is then filtered under reduced pressure, the residue is rinsed with 25 l of THF, and the filtrate is freed from solvent under reduced pressure. The crude product obtained in this way can be further reacted directly.

j) 2.89 g of the compound (12) obtained in accordance with i) are refluxed to hours with 10 ml of concentrated hydrochloric acid and 5 ml of water with stirring. The reaction solution is subsequently diluted with 50 ml of water and extracted with methyl t-butyl ether (3×30 ml). The aqueous phase is rendered alkaline using sodium hydroxide and extracted with dichloromethane (3×30 ml). The combined dichloromethane extracts are dried over sodium sulfate and freed from solvent. The residue obtained is dissolved in a little acetone, and ether/HCl is added. The crystalline precipitate formed is filtered off and subsequently dried at 50° C. under reduced pressure. Yield: 1.98 g; melting point: 121-130° C.

EXAMPLE 2

The following compounds can be obtained analogously to the processes described in Example 1:

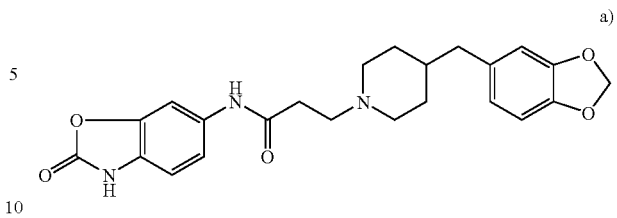

a)

3-[4-(3,4-methylenedioxybenzyl)piperidino]-N-(2-oxo-2,3-dihydrobenzoxazol-6-yl)propionamide

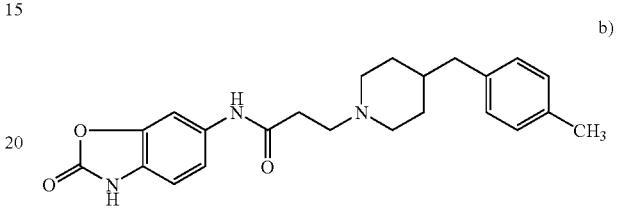

b)

3-[4-(4-methylbenzyl)piperidino]-N-(2-oxo-2,3-dihydrobenzoxazol-6-yl)propionamide

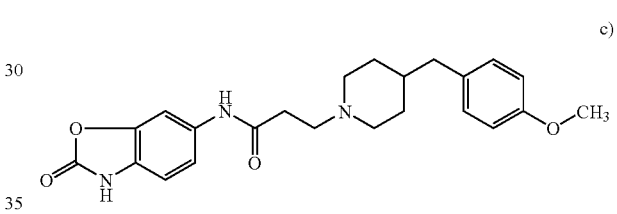

c)

3-[4-(4-methoxybenzyl)-1-piperidyl]-N-(2-oxo-2,3-dihydrobenzoxazol-6-yl)propionamide

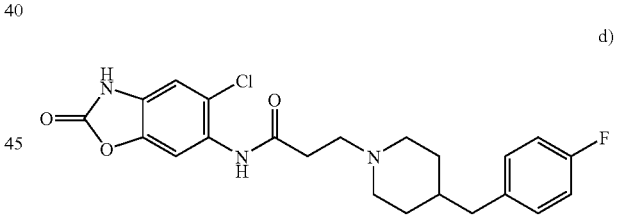

d)

5-chloro-6-[3-(4-(4-fluorobenzyl)-1-piperidyl)propionamido]-2,3-dihydrobenzoxazol-2-one

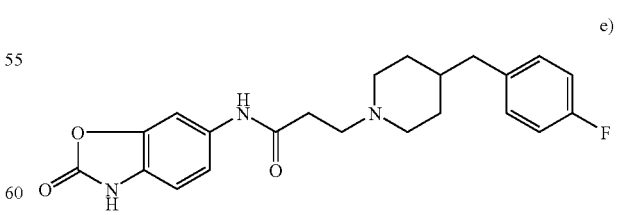

e)

3-[4-(4-fluorobenzyl)-1-piperidyl]-N-(2-oxo-2,3-dihydrobenzoxazol-6-yl)propionamide Physical constants and analytical data (mass spectrometric data (FAB-MS) and retention times (HPLC) of the compounds synthesised as above are shown in Table I.

TABLE I

| Structure | Molar mass | M.p. |
|---|---|---|
| (benzoxazolinone-NH-C(O)-CH2CH2-N(piperidine)-CH2-benzodioxole) | 459.93* | 236-8* |
| (benzoxazolinone-NH-C(O)-CH2CH2-N(piperidine)-CH2-C6H4-CH3) | 429.95* | 245-6* |
| (benzoxazolinone-NH-C(O)-CH2CH2-N(piperidine)-CH2-C6H4-OCH3) | 445.95* | 228-38* |
| (Cl-benzoxazolinone-NH-C(O)-CH2CH2-N(piperidine)-CH2-C6H4-F) | 431.90 | 158-61 |
| (benzoxazolinone-NH-C(O)-CH2CH2-N(piperidine)-CH2-C6H4-F) | 433.91* | 258-9* |

*Molar mass or melting point of the hydrochloride

EXAMPLE 3

2-Chloropropionyl chloride, dissolved dichloromethane, is added with stirring to a suspension of 5-aminobenzoxazolidinone in dichloromethane, and stirring is continued for 15 minutes at room temperature after the addition is complete. For work-up, the solvent is removed under reduced pressure, and the resultant residue is worked up by chromatographic methods, giving N-(2-oxo-2,3-dihydrobenzooxazol-6-yl)-2-chloropropionamide.

The resultant N-(2-oxo-2,3-dihydrobenzooxazol-6-yl)-2-chloropropionamide and 4-(4-fluorobenzyl)piperidine are dissolved in pyridine, and the mixture is subsequently heated at 120° C. for three hours with stirring. The solvent is subsequently removed under reduced pressure, and the residue is subjected to conventional work-up by partitioning the residue between a little water and methyl acetate. The aqueous phase is extracted with dichloromethane, the combined organic phases are dried over sodium sulfate, and the solvent is removed under reduced pressure. The residue obtained in this way is purified by chromatography (with dichloromethane/methanol in the ratio 97/3 as eluent), giving

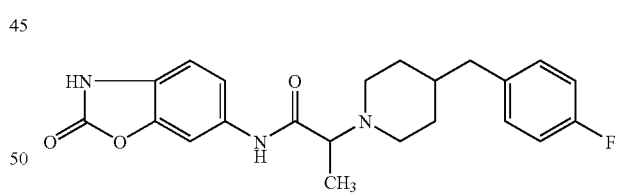

2-[4-(4-fluorobenzyl)piperidin-1-yl]-N-(2-oxo-2,3-dihydrobenzooxazol-6-yl)-propionamide.

EXAMPLE 4

The following compounds can be obtained analogously to the processes described in Example 3:

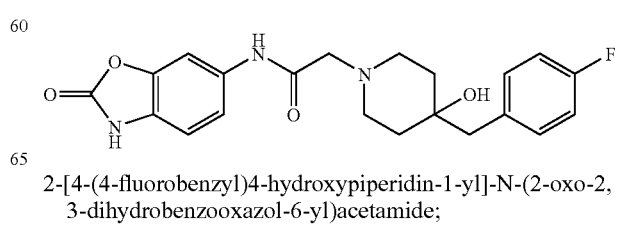

2-[4-(4-fluorobenzyl)4-hydroxypiperidin-1-yl]-N-(2-oxo-2,3-dihydrobenzooxazol-6-yl)acetamide;

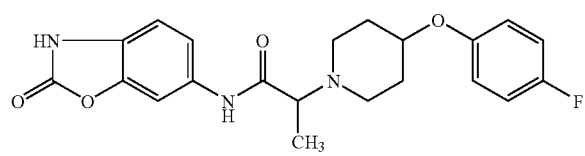

2-[4-(4-fluorophenoxy)piperidin-1-yl]-N-(2-oxo-2,3-dihydrobenzooxazol-6-yl)propionamide;

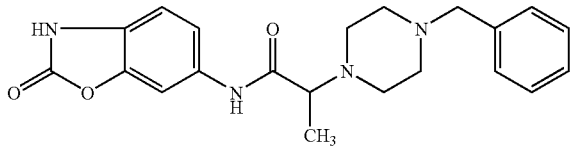

2-(4-benzylpiperazin-1-yl)-N-(2-oxo-2,3-dihydrobenzooxazol-6-yl)propionamide;

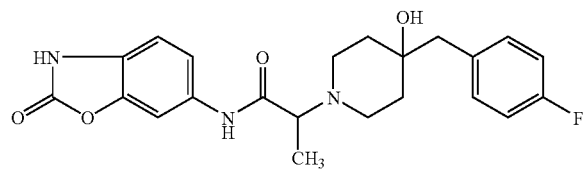

2-[4-(4-fluorobenzyl)-4-hydroxypiperidin-1-yl]-N-(2-oxo-2,3-dihydrobenzoxazol-6-yl)propionamide;

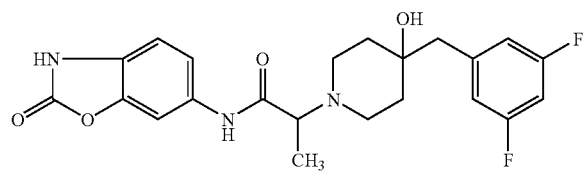

2-[4-(3,5-difluorobenzyl)4-hydroxypiperidin-1-yl]-N-(2-oxo-2,3-dihydrobenzoxazol-6-yl)propionamide.

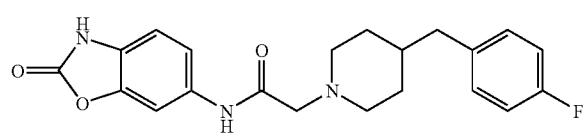

6-(2-(4-(4-fluorobenzyl)-1-piperidyl)acetamido)-2,3-dihydrobenzoxazol-2-one

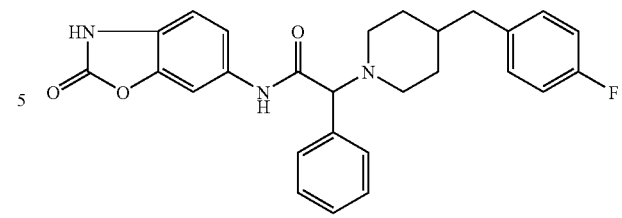

2-[4-(4-fluorobenzyl)piperidin-1-yl]-N-(2-oxo-2,3-dihydrobenzooxazol-6-yl)-2-phenylacetamides

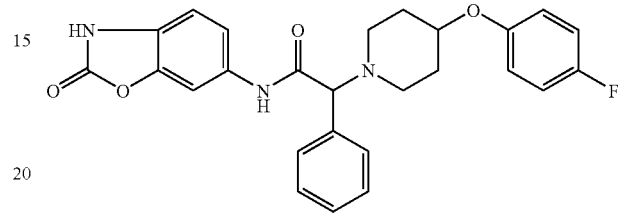

2-[4-(4-fluorophenoxy)piperidin-1-yl]-N-(2-oxo-2,3-dihydrobenzooxazol-6-yl)-2-phenylacetamides

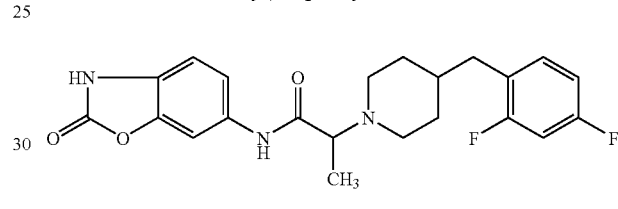

2-[4-(2,4-difluorobenzyl)piperidin-1-yl]-N-(2-oxo-2,3-dihydrobenzooxazol-6-yl)propionamides

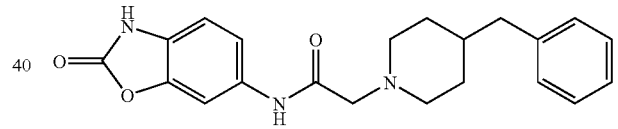

2-(4-benzyl-1-piperidyl)-N-(2-oxo-2,3-dihydrobenzoxazol-6-yl)acetamide

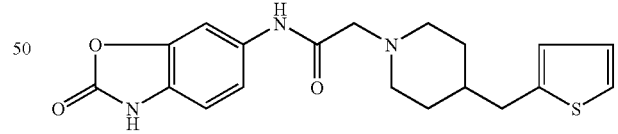

N-(2-oxo-2,3-dihydrobenzoxazol-6-yl)-2-(4-thiophen-2-ylmethyl-1-piperidyl)acetamide The compounds can be purified and/or characterised by HPLC chromatography. The characterisation of the compounds via the retention time ($R_t$) can be carried out on a 3μ Silica-Rod column with a 210 second gradient from 20 to 100% water/acetonitrile/0.01% trifluoroacetic acid at a flow rate of 2.2 ml/minute and detection at a wavelength of 220 nanometres.

Physical constants and analytical data (mass spectrometric data (FAB-MS) and retention times (HPLC)) of the compounds synthesised as above are shown in Table II.

TABLE II

| Structure | MW g/mol | FAB-MS [M + H] found | Rt(HPLC)/ min |
|---|---|---|---|
| (benzoxazolone-NH-C(O)-CH2-piperidine(4-OH)-CH2-C6H4-F) | 399.43 | 400.15 | 0.803 |
| (benzoxazolone-NH-C(O)-CH(CH3)-piperidine-4-O-C6H4-F) | 399.43 | 400.15 | 1.031 |
| (benzoxazolone-NH-C(O)-CH(CH3)-piperidine-4-CH2-C6H4-F) | 397.45 | 398.15 | 1.073 |
| (benzoxazolone-NH-C(O)-CH(CH3)-piperazine-N-CH2-C6H5) | 380.45 | 381.15 | 0.535 |
| (benzoxazolone-NH-C(O)-CH(CH3)-piperidine(4-OH)-CH2-C6H4-F) | 413.45 | 414.10 | 0.792 |
| (benzoxazolone-NH-C(O)-CH(CH3)-piperidine(4-OH)-CH2-C6H3-3,5-F2) | 431.44 | 432.05 | 0.883 |
| (benzoxazolone-NH-C(O)-CH2-piperidine-4-CH2-C6H4-F) | 383.43 | 384.2 | |
| (benzoxazolone-NH-C(O)-CH(C6H5)-piperidine-4-CH2-C6H4-F) | 459.52 | 460.2 | |

TABLE II-continued

| Structure | MW g/mol | FAB-MS [M + H] found | Rt(HPLC)/ min |
|---|---|---|---|
| 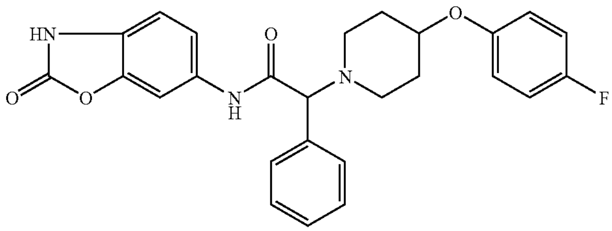 | 461.5 | 462.2 | |
| 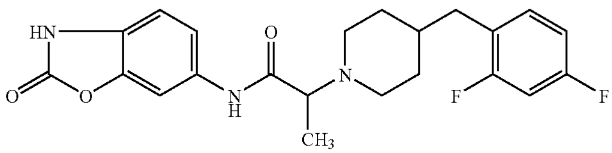 | 415.44 | 416.2 | |
| 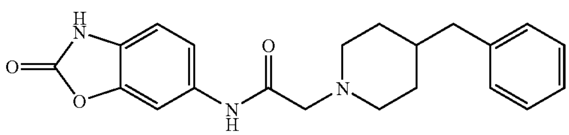 | 365.44 | 366.2 | |
| 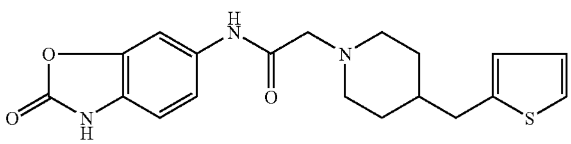 | 371.46 | 372.2 | |

EXAMPLE 5

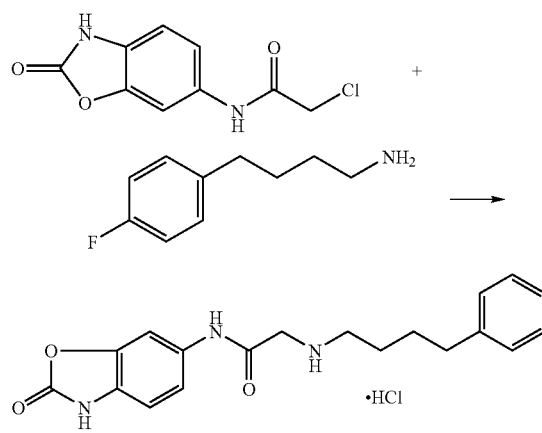

1.13 g of chloride (5) were suspended in 20 ml of acetonitrile in a 100 ml round-bottomed flask provided with magnetic stirrer, condenser and drying tube, 1.12 g of (4-F-phenyl)butylamine and 1.73 ml of triethylamine were added, and the mixture was stirred under reflux for 2 hours. The mixture was poured into water, extracted with dichloromethane, dried, filtered and stripped to dryness. The residue was chromatographed over silica gel with dichloromethane+4% methanol and crystallised from methanol/ether. The crystals were filtered off with suction and dried.

The base (0.41 g) was suspended in ethanol, ethereal HCl was added, during which a clear solution formed for a short time, and the crystallised salt was filtered off with suction and dried.

Yield: 230 mg (11.7%)

EXAMPLE 6

The following compounds can be obtained analogously to the process described in Example 5:

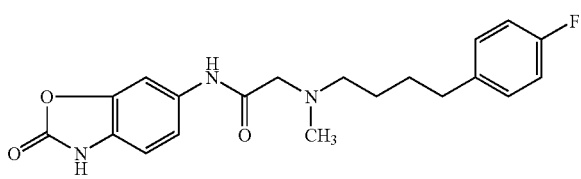

N-(2,3-dihydrobenzoxazol-6-yl)-2{N-[4-(4-fluorophenyl) butyl]-N-methylamino}acetamide.

The examples below relate to pharmaceutical compositions.

EXAMPLE A

Injection Vials

A solution of 100 g of the active ingredient of the formula I and 5 g of disodium hydrogenphosphate in 3 l of bidistilled water is adjusted to pH 6.5 using 2N hydrochloric acid, sterile filtered, transferred into injection vials, lyophilised under

EXAMPLE B

Suppositories

A mixture of 20 g of the active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of the active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of the active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

EXAMPLE I

Inhalation Spray 14 g of active ingredient of the formula I are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

The invention claimed is:

1. A compound of formula I

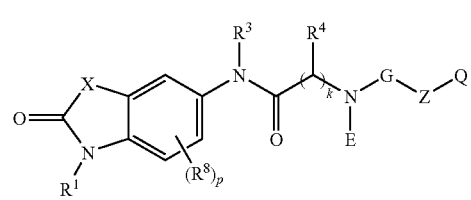

in which $R^1$ is H or A

A is straight-chain or branched alkyl having from 1 to 10 carbon atoms, alkenyl having from 2 to 10 carbon atoms, alkoxy having from 1 to 10 carbon atoms or alkoxyalkyl having from 2 to 10 carbon atoms, X is O, $R^2$ is H or A and $R^3$ is H, A, $(CH_2)_n$Het, $(CH_2)_n$Ar or cycloalkyl having from 3 to 7 carbon atoms, $R^4$ independently is H, A, cycloalkyl having from 3 to 7 carbon atoms, $(CH_2)_nNO_2$, $(CH_2)_n$Het, $(CH_2)_n$Ar, $(CH_2)_nCOR^6$, $(CH_2)_nCO(CH_2)_m$Ar, $(CH_2)_nCO(CH_2)_m$Het, $(CH_2)_nCOO(CH_2)_m$Ar, $(CH_2)_nCOO(CH_2)_m$Het, $(CH_2)_nOR^6$, $(CH_2)_nO(CH_2)_m$Ar, $(CH_2)_nO(CH_2)_m$Het, $(CH_2)_nSR^6$, $(CH_2)_nS(CH_2)_m$Ar, $(CH_2)_nS(CH_2)_m$Het, $(CH_2)_nN(R^6)(CH_2)_m$Ar, $(CH_2)_nN(R^6)(CH_2)_m$Het, $(CH_2)_nSO_2N(R^6)(CH_2)_m$Ar, $(CH_2)_nN(R^6)SO_2(CH_2)_m$Ar, $(CH_2)_nSO_2N(R^6)(CH_2)_m$Het, $(CH_2)_nN(R^6)SO_2(CH_2)_m$Het, $(CH_2)_nCON(R^6)(CH_2)_m$Ar, $(CH_2)_nN(R^6)CO(CH_2)_m$Ar, $(CH_2)_nCON(R^6)(CH_2)_m$Het, $(CH_2)_nN(R^6)CO(CH_2)_m$Het, $(CH_2)_nN(R^6)_2$, CH=N—OA, $CH_2CH=N$—OA, $(CH_2)_n$NHOA, $(CH_2)_n(R^6)$Het, $(CH_2)_nCH=N$-Het, $(CH_2)_nOCOR^6$, $(CH_2)_nOC(O)N(R^6)_2$, $(CH_2)_nOC(O)NR^6$, $(CH_2)_mAr$, $(CH_2)_nOC(O)NR^6(CH_2)_m$Het, $(CH_2)_nNR^6COOR^6$, $(CH_2)_nNR^6COO(CH_2)_m$Ar, $(CH_2)_nNR^6COO(CH_2)_m$Het, $(CH_2)_nN(R^6)CH_2CH_2OR^6$, $(CH_2)_nN(R^6)CH_2CH_2OCF_3$, $(CH_2)_nN(R^6)C(R^6)HCOOR^6$, $(CH_2)_nN(R^6)CH_2COHet$, $(CH_2)_nN(R^6)CH_2Het$, $(CH_2)_nN(R^6)CH_2CH_2N(R^6)CH_2COOR^6$, $(CH_2)_nN(R^6)CH_2CH_2N(R^6)_2$, CH=CHCOOR^6$, CH=CHCH_2NR^6Het$, CH=CHCH_2N(R^6)_2$, CH=CHCH_2OR^6$, $(CH_2)_nN(COOR^6)COOR^6$, $(CH_2)_nN(CONH_2)COOR^6$, $(CH_2)_nN(CONH_2)CONH_2$, $(CH_2)_nN(CH_2COOR^6)COOR^6$, $(CH_2)_nN(CH_2CONH_2)COOR^6$, $(CH_2)_nN(CH_2CONH_2)CONH_2$, $(CH_2)_nCHR^6COR^6$, $(CH_2)_nCHR^6COOR^6$, $(CH_2)_nCHR^6CH_2OR^6$, $(CH_2)_nOCN$ or $(CH_2)_nNCO$, $R^6$ is H, A or cycloalkyl having from 3 to 7 carbon atoms, and k is 2, E and G, together with the N atom to which they are bonded, is a 6-membered heterocyclic radical, Z is O, S, N—R$^{15}$, CH$_2$ or CH$_2$CH$_2$, R$^{15}$ is H, A, (CH$_2$)$_n$Het, (CH$_2$)$_n$Ar or cycloalkyl having from 3 to 7 carbon atoms, Het is a saturated, unsaturated or aromatic mono- or bicyclic heterocyclic radical which is unsubstituted or mono- or polysubstituted by A, Hal, NO$_2$, CN, OR$^6$, N(R$^6$)$_2$, COOR$^6$, CON(R$^6$)$_2$, NR$^6$COR$^6$, NR$^6$CON(R$^6$)$_2$, NR$^6$SO$_2$A, COR$^6$, SO$_2$NR$^6$, S(O)$_w$A and/or OOCR$^6$, Ar is an aromatic hydrocarbon radical having from 6 to 14 carbon atoms which is unsubstituted or mono- or polysubstituted by A, Hal, NO$_2$, CN, OR$^6$, N(R$^6$)$_2$, COOR$^6$, CON(R$^6$)$_2$, NR$^6$COR$^6$, NR$^6$CON(R$^6$)$_2$, NR$^6$SO$_2$A, COR$^6$, SO$_2$NR$^6$, S(O)$_w$A and/or OOCR$^6$, p is 0, 1, 2 or 3 w is 0, 1, 2 or 3

Hal is F, Cl, Br or I,

Q is a 5- or 6-membered, polyethylenically unsaturated or aromatic carbocyclic or heterocyclic radical, which be mono- or polysubstituted, where the substituents are selected, independently of one another, from the meanings of R$^4$ other than H, and where the heterocyclic radical can contain from 1 to 4 N, O and S atoms, or pharmaceutically usable salt thereof.

2. A compounds of the formula I according to claim 1, which is of formula Ia in which q is 1, Y is CH, —C—O—R$^7$, —C—S—R$^7$, or N, and R$^7$ independently are H, A, (CH$_2$)$_n$Het, (CH$_2$)$_n$Ar or cycloalkyl having from 3 to 7 carbon atoms, or pharmaceutically usable salt thereof.

3. A compounds according to claims 1, in which Z-Q is in which the radicals

R$^{10}$ independently are selected from the meanings of R$^4$ other than H, or, independently of one another, are A, Hal, NO$_2$, OR$^6$, N(R$^6$)$_2$, CN, COOR$^6$, CON(R$^6$)$_2$, NR$^6$COR$^6$, NR$^6$CON(R$^6$)$_2$, NR$^6$SO$_2$A, COR$^6$, SO$_2$NR$^6$, S(O)$_w$A, OOCR$^6$ and/or C(NH)NOH, and r is 0, 1, 2, 3, 4 or 5.

4. A process for the preparation of a compound of formula I according to claim 1 or a salt thereof, comprising
a) a compound of the formula II in which L$^1$ is H or a metal ion, and R$^1$, X, R$^3$, R$^8$ and p are as defined in formula I, b) is reacted with a compound of the formula V in which L$^2$ is Cl, Br, I, OH or a reactively esterified OH group, L$^3$ is Cl, Br, I, OH or a diazonium group and R$^4$ and k are as defined in formula I, and subsequently a product thereof is c) with a compound of the formula VI in which L$^4$ is H or a metal ion, and E, G, Z, and Q are as defined for the compound of formula I, and, optionally, d) the resultant compound of the formula I is converted into one of its salts by treatment with an acid.

5. A process for the preparation of a pharmaceutical composition, comprising converting a compound of the formula I according to claim 1 and/or a physiologically acceptable salt thereof into a suitable dosage form together with at least one solid, liquid or semi-liquid excipient or adjuvant.

6. A compound according to claim 1, which is a) 3-[4-(3,4-methylenedioxybenzyl)piperidino]-N-(2-oxo-2,3-dihydro-benzoxazol-6-yl)propionamide b) 3-[4-(4-methylbenzyl)piperidino]-N-(2-oxo-2,3-dihydrobenzoxazol-6-yl)propionamide c) 3-[4-(4-methoxybenzyl)-1-piperidyl]-N-(2-oxo-2,3-dihydrobenzoxazol-6-yl)propionamide d) 5-chloro-6-[3-(4-(4-fluorobenzyl)-1-piperidyl)propionamido]-2,3-di-hydrobenzoxaxol-2-one e) 3-[4-(4-fluorobenzyl)-1-piperidyl]-N-(2-oxo-2,3-dihydrobenzoxazol-6-yl)propionamide or f) N-(2,3-dihydro-2-oxo-6-benzoxazolyl)-3-[4-(4-fluorobenzyl)-1-piperidyl]propionamide.

7. A pharmaceutical composition, comprising an effective amount of at least one compound of formula I according to claim 1 and/or a physiologically acceptable salt thereof and a pharmaceutically acceptable carrier.

8. A method for treating a neurodegenerative disease, comprising administering, to a host in need thereof an NMDA receptor antagonistic effective amount of, a compound according to claim 1 or a pharmaceutically useable salt thereof.

9. A method for treating a cerebrovascular disease, epilepsy, schizophrenia, Alzheimer's disease, Parkinson's disease, Huntington's disease, cerebral ischaemia, or psychoses, comprising administering, to a host in need thereof an NMDA receptor antagonistic effective amount of, a compound according to claim 1 or a pharmaceutically useable salt thereof.

10. A method for treating epilepsy, schizophrenia, Parkinson's disease, Huntington's disease, cerebral ischaemia, or psychoses, comprising administering, to a host in need thereof an NMDA receptor antagonistic effective amount of, a compound according to claim 1 or a pharmaceutically useable salt thereof.

* * * * *